United States Patent
Heneghan et al.

(10) Patent No.: US 10,799,126 B2
(45) Date of Patent: Oct. 13, 2020

(54) APPARATUS, SYSTEM AND METHOD FOR CHRONIC DISEASE MONITORING

(71) Applicant: ResMed Sensor Technologies Limited, Dublin (IE)

(72) Inventors: Conor Heneghan, San Diego, CA (US); Alberto Zaffaroni, Dublin (IE); Philip De Chazal, Dublin (IE); Redmond Shouldice, Dublin (IE)

(73) Assignee: ResMed Sensor Technologies Limited (IE)

( * ) Notice: Subject to any disclaimer, the term of this patent is extended or adjusted under 35 U.S.C. 154(b) by 659 days.

(21) Appl. No.: 15/343,994

(22) Filed: Nov. 4, 2016

(65) Prior Publication Data

US 2017/0231504 A1  Aug. 17, 2017

Related U.S. Application Data

(63) Continuation of application No. 12/367,255, filed on Feb. 6, 2009, now Pat. No. 9,526,429.

(51) Int. Cl.
*A61B 5/0205* (2006.01)
*A61B 5/00* (2006.01)
(Continued)

(52) U.S. Cl.
CPC .............. *A61B 5/0205* (2013.01); *A61B 5/08* (2013.01); *A61B 5/0826* (2013.01); *A61B 5/113* (2013.01);
(Continued)

(58) Field of Classification Search
CPC ....... A61B 5/0205; A61B 5/08; A61B 5/0826; A61B 5/113; A61B 5/411; A61B 5/4818;
(Continued)

(56) References Cited

U.S. PATENT DOCUMENTS 2,634,413 A  4/1953  Potter
3,796,208 A  3/1974  Bloice
(Continued)

FOREIGN PATENT DOCUMENTS

CN  1723842 A  1/2006
CN  101108125 A  1/2008
(Continued)

OTHER PUBLICATIONS

Wang Yongqing, "Principle and Methodology of Artificial Intelligence", Xi'An Jiaotong University Press, Jul. 1999, pp. 325 to 326.
(Continued)

*Primary Examiner* — Michael W Kahelin
*Assistant Examiner* — Vynn V Huh
(74) *Attorney, Agent, or Firm* — Botos Churchill IP Law LLP

(57) ABSTRACT

An apparatus, system, and method for monitoring a person suffering from a chronic medical condition predicts and assesses physiological changes which could affect the care of that subject. Examples of such chronic diseases include (but are not limited to) heart failure, chronic obstructive pulmonary disease, asthma, and diabetes. Monitoring includes measurements of respiratory movements, which can then be analyzed for evidence of changes in respiratory rate, or for events such as hypopneas, apneas and periodic breathing. Monitoring may be augmented by the measurement of nocturnal heart rate in conjunction with respiratory monitoring. Additional physiological measurements can also be taken such as subjective symptom data, blood pressure, blood oxygen levels, and various molecular markers. Embodiments for detection of respiratory patterns and heart rate are disclosed, together with exemplar implementations of decision processes based on these measurements.

42 Claims, 19 Drawing Sheets

(51) Int. Cl.
  G16H 50/30 (2018.01)
  G16H 50/20 (2018.01)
  A61B 5/08 (2006.01)
  G01S 13/50 (2006.01)
  A61B 5/113 (2006.01)
  A61B 5/024 (2006.01)
  A61B 5/05 (2006.01)
  A61B 5/145 (2006.01)
  A61B 6/00 (2006.01)

(52) U.S. Cl.
  CPC ............ *A61B 5/411* (2013.01); *A61B 5/4818* (2013.01); *A61B 5/7264* (2013.01); *A61B 5/7282* (2013.01); *A61B 5/742* (2013.01); *G01S 13/50* (2013.01); *G16H 50/20* (2018.01); *G16H 50/30* (2018.01); *A61B 5/024* (2013.01); *A61B 5/0507* (2013.01); *A61B 5/0816* (2013.01)

(58) Field of Classification Search
  CPC ..... A61B 5/7264; A61B 5/7282; A61B 5/742; A61B 5/024; A61B 5/0507; A61B 5/0816; G16H 50/30; G16H 50/20; G01S 13/50; G06F 19/00
  See application file for complete search history.

(56) References Cited

U.S. PATENT DOCUMENTS

| | | | |
|---|---|---|---|
| 3,911,899 A | 10/1975 | Hattes | |
| 3,993,995 A | 11/1976 | Kaplan et al. | |
| 4,085,740 A | 4/1978 | Allen, Jr. | |
| 4,513,748 A | 4/1985 | Nowogrodzki et al. | |
| 4,958,638 A * | 9/1990 | Sharpe | A61B 5/0205 600/407 |
| 5,203,343 A | 4/1993 | Axe et al. | |
| 5,314,037 A | 5/1994 | Shaw et al. | |
| 5,339,821 A | 8/1994 | Fujimoto | |
| 5,361,070 A | 11/1994 | McEwan | |
| 5,519,400 A | 5/1996 | McEwan | |
| 5,521,600 A | 5/1996 | McEwan | |
| 5,549,113 A | 8/1996 | Halleck et al. | |
| 5,573,012 A | 11/1996 | McEwan | |
| 5,590,650 A | 1/1997 | Genova | |
| 5,671,733 A | 9/1997 | Raviv et al. | |
| 5,682,164 A | 10/1997 | McEwan | |
| 5,766,208 A | 6/1998 | McEwan | |
| 5,828,333 A | 10/1998 | Richardson et al. | |
| 5,902,250 A | 5/1999 | Verrier et al. | |
| 5,944,680 A * | 8/1999 | Christopherson | A61B 5/03 128/897 |
| 5,966,090 A | 10/1999 | McEwan | |
| 5,999,846 A | 12/1999 | Pardey et al. | |
| 6,011,477 A | 1/2000 | Teodorescu et al. | |
| 6,062,216 A | 5/2000 | Corn | |
| 6,132,371 A | 10/2000 | Dempsey et al. | |
| 6,146,332 A | 11/2000 | Pinsonneault et al. | |
| 6,358,201 B1 | 3/2002 | Childre et al. | |
| 6,359,597 B2 | 3/2002 | Haj-Yousef | |
| 6,426,716 B1 | 7/2002 | McEwan | |
| 6,492,933 B1 | 12/2002 | McEwan | |
| 6,661,345 B1 | 12/2003 | Bevan et al. | |
| 6,834,251 B1 | 12/2004 | Fletcher | |
| 6,839,581 B1 | 1/2005 | El-Solh et al. | |
| 6,932,769 B2 | 8/2005 | Griffin et al. | |
| 7,196,629 B2 | 3/2007 | Ruoss et al. | |
| 7,199,749 B2 | 4/2007 | Greneker, III et al. | |
| 7,272,431 B2 | 9/2007 | McGrath | |
| 7,387,607 B2 | 6/2008 | Holt et al. | |
| 7,428,468 B2 | 9/2008 | Takemura et al. | |
| 7,468,034 B2 | 12/2008 | Ouchi | |
| 7,473,228 B2 | 1/2009 | Griffin et al. | |
| 7,679,545 B2 | 3/2010 | Rausch et al. | |
| 7,898,455 B2 | 3/2011 | Rosenbury | |
| 7,956,755 B2 | 6/2011 | Lee et al. | |
| 8,026,840 B2 | 9/2011 | Dwelly et al. | |
| 8,398,538 B2 | 3/2013 | Dothie et al. | |
| 8,428,696 B2 | 4/2013 | Foo | |
| 8,454,528 B2 | 6/2013 | Yuen et al. | |
| 8,562,526 B2 | 10/2013 | Heneghan et al. | |
| 2002/0088465 A1 | 7/2002 | Hill | |
| 2003/0092975 A1 | 5/2003 | Casscells et al. | |
| 2003/0144829 A1 | 7/2003 | Geatz et al. | |
| 2003/0201894 A1 | 10/2003 | Li | |
| 2004/0012447 A1 | 1/2004 | Nagaishi et al. | |
| 2004/0073098 A1 | 4/2004 | Geva et al. | |
| 2004/0116981 A1 * | 6/2004 | Mazar | A61N 1/08 607/60 |
| 2004/0123667 A1 | 7/2004 | McGrath | |
| 2004/0230105 A1 | 11/2004 | Geva et al. | |
| 2004/0249258 A1 | 12/2004 | Tupin et al. | |
| 2004/0249296 A1 | 12/2004 | Ellscheid et al. | |
| 2005/0042589 A1 | 2/2005 | Hatlestad et al. | |
| 2005/0043645 A1 | 2/2005 | Ono et al. | |
| 2005/0073424 A1 | 4/2005 | Ruoss et al. | |
| 2005/0085738 A1 | 4/2005 | Stahmann et al. | |
| 2005/0113711 A1 | 5/2005 | Nakatani | |
| 2005/0119532 A1 | 6/2005 | Cloutier | |
| 2005/0119711 A1 | 6/2005 | Cho et al. | |
| 2005/0128124 A1 | 6/2005 | Greneker et al. | |
| 2005/0143617 A1 | 6/2005 | Auphan | |
| 2005/0240087 A1 | 10/2005 | Keenan et al. | |
| 2006/0038689 A1 | 2/2006 | Ikegami et al. | |
| 2006/0047213 A1 | 3/2006 | Gavriely et al. | |
| 2006/0079164 A1 | 4/2006 | DeCastro et al. | |
| 2006/0111635 A1 | 5/2006 | Todros et al. | |
| 2006/0155175 A1 | 7/2006 | Ogino et al. | |
| 2006/0187111 A1 | 8/2006 | Uchino | |
| 2006/0189924 A1 | 8/2006 | Blakley et al. | |
| 2006/0241359 A1 | 10/2006 | Nagai et al. | |
| 2006/0241510 A1 | 10/2006 | Halperin et al. | |
| 2006/0270941 A1 | 11/2006 | Xie et al. | |
| 2007/0021979 A1 | 1/2007 | Cosentino et al. | |
| 2007/0027367 A1 | 2/2007 | Oliver et al. | |
| 2007/0083079 A1 | 4/2007 | Lee et al. | |
| 2007/0106129 A1 | 5/2007 | Srivathsa et al. | |
| 2007/0118054 A1 | 5/2007 | Pinhas et al. | |
| 2007/0161917 A1 | 7/2007 | Ozaki et al. | |
| 2007/0239057 A1 | 10/2007 | Pu et al. | |
| 2008/0074307 A1 | 3/2008 | Boric-Lubecke et al. | |
| 2008/0076997 A1 | 3/2008 | Peyser et al. | |
| 2008/0157956 A1 | 7/2008 | Radivojevic et al. | |
| 2008/0234568 A1 | 9/2008 | Ouchi | |
| 2008/0238757 A1 | 10/2008 | Lin et al. | |
| 2008/0269589 A1 | 10/2008 | Thijs et al. | |
| 2008/0269625 A1 | 10/2008 | Halperin et al. | |
| 2009/0076405 A1 | 3/2009 | Amurthur | |
| 2009/0256739 A1 | 10/2009 | Teshirogi et al. | |
| 2010/0049008 A1 | 2/2010 | Doherty et al. | |
| 2011/0015495 A1 | 1/2011 | Dothie et al. | |
| 2011/0034811 A1 | 2/2011 | Naujokat et al. | |
| 2011/0112425 A1 | 5/2011 | Muhlsteff et al. | |
| 2011/0288379 A1 | 11/2011 | Wu | |
| 2012/0245479 A1 | 9/2012 | Ganesh et al. | |
| 2013/0006124 A1 | 1/2013 | Eyal et al. | |
| 2013/0053653 A1 | 2/2013 | Cuddihy et al. | |
| 2013/0135137 A1 | 5/2013 | Mulder et al. | |
| 2013/0172770 A1 | 7/2013 | Muehlsteff | |
| 2014/0350361 A1 | 11/2014 | De Ghazal et al. | |
| 2017/0179771 A1 | 6/2017 | Leabman | |
| 2018/0239014 A1 | 8/2018 | McMahon | |

FOREIGN PATENT DOCUMENTS

| | | |
|---|---|---|
| CN | 101332329 A | 12/2008 |
| JP | 64-027535 A | 1/1989 |
| JP | H08275927 A | 10/1996 |
| JP | H10155749 A | 6/1998 |
| JP | 2000083927 A | 3/2000 |
| JP | 2004252770 A | 9/2004 |
| JP | 2004526470 A | 9/2004 |
| JP | 2005152328 A | 6/2005 |

(56) References Cited

FOREIGN PATENT DOCUMENTS

| | | |
|---|---|---|
| JP | 2005270570 A | 10/2005 |
| JP | 2006055501 A | 3/2006 |
| JP | 2006510451 A | 3/2006 |
| JP | 2007007149 A | 1/2007 |
| JP | 2007502670 A | 2/2007 |
| JP | 2007075586 A | 3/2007 |
| JP | 2007181613 A | 7/2007 |
| JP | 2008110138 A | 5/2008 |
| JP | 2009501557 A | 1/2009 |
| JP | 2010508128 A | 3/2010 |
| WO | 97/14354 A2 | 4/1997 |
| WO | 2004114193 A2 | 12/2004 |
| WO | 2005018737 A1 | 3/2005 |
| WO | 2005028029 A2 | 3/2005 |
| WO | 2006048852 A1 | 5/2006 |
| WO | 2006137067 A2 | 12/2006 |
| WO | 2007143535 A2 | 12/2007 |
| WO | 2008046190 A1 | 4/2008 |
| WO | 2008057883 A2 | 5/2008 |
| WO | 2008096307 A1 | 8/2008 |
| WO | 2009124297 A1 | 10/2009 |
| WO | 2009127799 A1 | 10/2009 |
| WO | 2010048310 A1 | 4/2010 |
| WO | 2010132850 A1 | 11/2010 |
| WO | 2012073183 A1 | 6/2012 |
| WO | 2013093712 A1 | 6/2013 |

OTHER PUBLICATIONS

Office Action in Ex Parte Reexamination issued in correspondino U.S. Appl. No. 96/000,275 dated Dec. 7, 2018.
"The Fundamentals of FFT-Based Signal Analysis and Measurement in LabVIEW and LabWindows/CVI" National Instruments, Published Jun. 8, 2009. 12 pages. Accessed Jan. 26, 2012. URL: http://zonetni.com/devzone/cda/tut/p/id/4278#toc0.
Australian Examination Report for Application No. 2007256872 dated Mar. 20, 2012.
Australian Examination Report for Application No. 2010210569 dated Mar. 12, 2014.
Chinese Office Action for Application No. 201080012088.9 dated Jan. 6, 2014.
Chinese Office Action for Application No. 201080012088.9 dated Sep. 3, 2013.
Droitcour et al., "Range Correlation and Iiq Performance Benefits in Single-Chip Silicon Doppler Radars for Noncontact Cardiopulmonary Monitoring", IEEE Transactions on Microwave Theory and Techniques, Mar. 3, 2004, vol. 52, No. 3, pp. 838-848.
European Search Report and Search Opinion for European Patent Application No. 07784266A, dated Oct. 7, 2010.
Intenational Search Report for PCT International Application No. PCT/US2007/070196, dated Feb. 22, 2008.
International Preliminary Report on Patentability dated May 26, 2011 of PCT/US2010/023177 filed Feb. 4, 2010 (13 pages).
International Preliminay Report on Patentability for PCT International Application No. PCT/US2007/070196, dated Dec. 3, 2008.
International Search Report and Written Opinion for PCT International Patent Application No. PCT/US2010/023177, dated on Jul. 23, 2010.
International Search Report and Written Opinion of the International Searching Authority for PCT International Application No. PCT/US2007/070196, dated Feb. 22, 2008.
International Search Report and Written Opinion of the International Searching Authority for PCT International Application No. PCT/US2007/083155, dated Mar. 7, 2010.
Invitation to Pay Additional fees and Partial International Search Report for PCT International Patent Application No. PCT/US2010/023177, dated Jun. 7, 2010.
Japanese Office Action for Application No. 2011549255 dated Feb. 28, 2014.
Second Office Action dated Apr. 14, 2011 of Chinese Application No. 200780026740.0 filed Jan. 14, 2009 (16 pages).
JP Office Action dated Apr. 26, 2012—JP Application No. 2009513469.
JP Office Action dated Aug. 11, 2011—JP Application No. 2009513469.
JP Office Action dated Nov. 19, 2012—JP Application No. 2009513469.
JP Office Action dated Oct. 13, 2011—JP Application No. 2009513469.
Office Action dated Feb. 1, 2012—U.S. Appl. No. 12/302,704.
Office Action dated Jan. 30, 2013—U.S. Appl. No. 12/302,704.
Office Action dated Jul. 16, 2012—U.S. Appl. No. 12/302,704.
Office Action dated Sep. 16, 2011—U.S. Appl. No. 12/302,704.
Watanabe, Kajiro , et al., "Estimation of Sleep Stages Based on Heart Rate Fluctuation and Body Movement", Hokkaido Institute of Technology, Japan. SICE Annual Conference in Sapporo, Aug. 4-6, 2004.

* cited by examiner

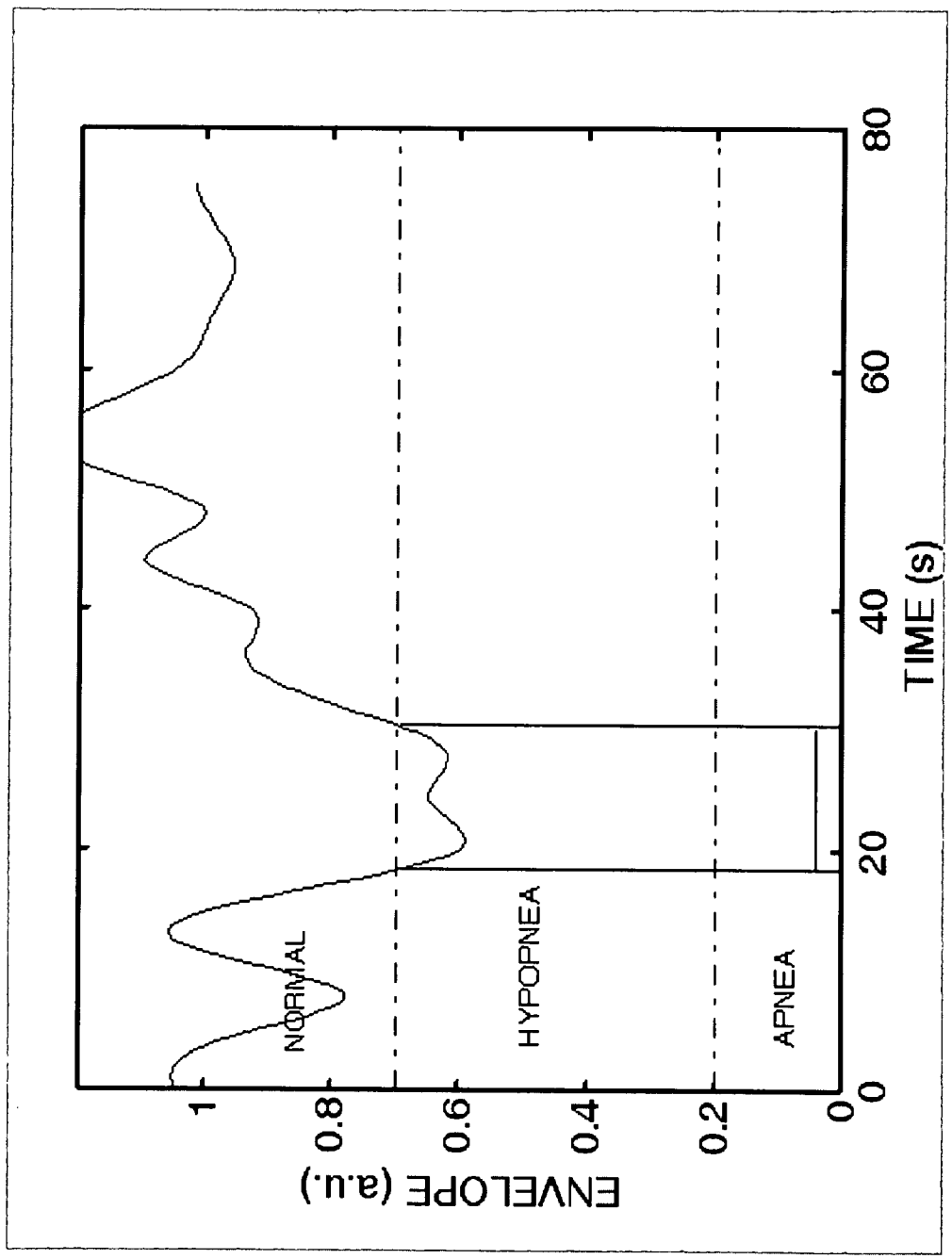

APPARATUS, SYSTEM AND METHOD FOR CHRONIC DISEASE MONITORING

CROSS-REFERENCE TO RELATED APPLICATIONS

The present application is a continuation of U.S. application Ser. No. 12/367,255, which was filed on Feb. 6, 2009 and issued as U.S. Pat. No. 9,526,429.

BACKGROUND

This disclosure relates to a system for monitoring a person suffering from a chronic medical condition in order to predict and assess physiological changes which could affect the care of that subject. Examples of such chronic diseases include (but are not limited to) heart failure, chronic obstructive pulmonary disease (COPD), asthma, and diabetes.

To provide a context for the limitations of conventional approaches, it is instructive to briefly review current approaches to chronic disease monitoring for three major diseases: heart failure, COPD and asthma.

Heart failure (HF) is a relatively common and severe clinical condition, characterized by the inability of the heart to keep up with the oxygen demands of the body. Management of heart failure is a significant challenge to modern healthcare systems due to its high prevalence and severity. It is estimated that heart failure accounts for approximately 2-3% of the entire healthcare budget of developed nations, and is the number one cause of hospitalization of the over-65 s in the USA.

Heart failure is a chronic condition, which is progressive in nature. Physicians typically class the severity of the disease according to a New York Heart Association (NYHA) subjective grading system from 1 to 4, where 4 is the most severe case. Heart failure can also be further broken into classes such as systolic and diastolic heart failure. The progression of heart failure is often characterized as relatively stable over long periods of time (albeit with reduced cardiovascular function) punctuated by episodes of an acute nature. In this acute phases, the patient experiences worsening of symptoms such as dyspnea (difficulty breathing), gallop rhythms, increased jugular venous pressure, and orthopnea. This is typically accompanied by overt congestion (which is the build up of fluid in the pulmonary cavity). This excess fluid often leads to measurable weight gain of several kilograms. In many cases, however, by the time overt congestion has occurred, there are limited options for the doctor to help restabilize the patients, and in many cases the patient requires hospitalization.

There already exist some approaches to the detection of clinical deterioration, but with limitations. For example, a range of chronic disease management programs have been developed to improve the healthcare response to HF, with an emphasis on both increased patient care and reduced cost. Critical components of successful programs include a) patient education, b) telemonitoring of physiological measurements and symptoms, c) sophisticated decision support systems to use the reported symptoms and measurements to predict clinically significant events, and d) a focus on individualized care and communication (e.g., "teaching in the moment" in response to events affecting a patient's health).

However, accurate diagnosis of clinical deterioration in heart failure can be quite difficult. In particular, prevention of overt congestion which often requires hospitalization, is of particular importance. Weight measurement has been shown to be a reasonably reliable physiological guide to heart failure deterioration. This can lead to reduced mortality, when combined with other accepted strategies for heart failure management. Moreover, weight management has the additional psychological benefit of involving the patient directly in their own care, as well as being simple and low-cost.

However, despite the widespread use of recommendations on weight gain as a marker of deterioration (e.g., a patient is told that a gain of 2 kg over a 2 to 3 day period should generate a call to their clinic), there is relatively little published data on the sensitivity and specificity of ambulatory monitoring of weight gain in a clinical setting. Groups who have investigated the sensitivity of weight gain in distinguishing clinically stable (CS) Class IV patients from those with clinical deterioration (CD), have found that the performance is quite limited. These researchers found quite modest predictive values for weight gain in isolation. For example, the clinical guideline of 2 kg weight gain over 48-72 h has a specificity of 97% but a sensitivity of only 9%. Reducing the threshold to 2% of body weight, improves the sensitivity to 17% (with specificity only dropping marginally). In general they conclude that weight gain in isolation has relatively poor sensitivity in detecting clinical deterioration (though its specificity is good).

Thus, what is needed is a system and method to overcome the current limitation on the sensitivity of weight gain to predict clinical deterioration.

Measurement of B natriuretic peptides (BNP) has also been suggested as a viable tool for assessment of heart failure status; this could be implemented at a primary care or outpatient clinic setting using point-of-care devices, though at present it cannot be clinically deployed on a daily monitoring basis. In a report on BNP monitoring, researchers reported a sensitivity of 92% on a population of 305 subjects, but with a specificity of only 38%. While this is a promising approach, there are significant practical issues around providing point-of-care assays for BNP in community care due to cost, training and patient convenience. Accordingly, there remains a need for development of improved low-cost convenient diagnostic markers of clinical deterioration of heart failure which can be deployed in the patient's day-to-day environment.

Thus, what is needed is a system and method to improve the specificity of detecting clinical deterioration as compared to approaches such as BNP monitoring, and for such systems to be convenient for patient use in their home environment.

Some potential markers of clinical deterioration in heart failure are changes in nocturnal heart rate, changes in sleeping posture, and changes in respiration. In particular, heart failure is highly correlated with sleep disordered breathing (SDB), though the causality mechanisms are not well understood. For example, in a recent study in Germany, 71% of heart failure patients have an Apnea-Hypopnea index greater than 10 per hour (with 43% having obstructive sleep apnea and 28% having primarily Cheyne-Stokes respiration (periodic breathing). Other researchers reported a prevalence of 68% in their HF population in a New Zealand study. Significant sleep disordered breathing has been reported to correlate with poor outcomes in heart failure; however, no study has yet been able to track changes in respiratory patterns over time to see how it varies with clinical stability. For example, in the Home or Hospital in Heart Failure (HHH) European-wide study, overnight respiratory recording (using respiratory inductance plethysmography) was carried out for a single night at baseline in 443 clinically stable HF patients. Apnea Hypopnea Index and Duration of Periodic Breathing were shown to be independent predictors of cardiac death and hospitalization for clinical deterioration. However no practical system for assessing these respiratory parameters on a nightly basis was available for these researchers.

Measurement of nocturnal heart rate and heart rate variability can also aid in the detection of clinical deterioration in heart failure.

A second chronic medical condition for which the current system can be used is Chronic Obstructive Pulmonary Disease (COPD). COPD is a disease of the lungs in which the airways are narrowed, which leads to a restricted flow of air to the lungs. COPD is currently the fourth leading cause of death in the USA, and its estimated cost to the healthcare system is $42.6 billion in 2007. It is associated with dyspnea (shortness of breath) and elevated breathing rates (tachypnea). As for heart failure, there can be acute exacerbations of COPD, often due to bacterial or viral infections. However, definitions of what exactly constitutes an exacerbation, and means to accurately predict it are a subject of active research in the medical community. For example, tracking of C-reactive protein or measurements of inspiratory capacity have been proposed as means to predict exacerbations. Changes in peak expiratory flow have been considered for prediction of clinical deterioration, but are considered insufficiently sensitive.

Thus what is needed is a reliable method for accurately recognizing exacerbations in COPD patients. Further, what is needed is a system and method for recognizing clinical deterioration in COPD patients through tracking of respiratory patterns.

Respiratory rate is a key indicator of the severity of COPD. For example, normal healthy adults may have respiratory rates which are about 14-16 breaths/minute while asleep; the resting respiratory rate of a person with severe COPD (but not in acute respiratory failure) may be in the range 20-25 breaths/minute, while in an acute respiratory failure, this rate may increase to more than 30 breaths/minute. Accordingly a system for simple monitoring of respiratory rate has utility in assessing the status of subjects with COPD. However, current systems for monitoring respiratory rate are typically based on measurement of airflow using nasal cannulae or respiratory effort belts and are not used for continuous monitoring of respiratory patterns in the person's own environment due to comfort and convenience issues. Thus what is needed is a system for tracking exacerbations in COPD patients which does not require the subject to wear an oro-nasal cannula or chest belt.

An additional chronic medical condition is asthma. This is a common chronic condition in which the airways occasionally constrict, become inflamed, and are lined with excessive amounts of mucus, often in response to one or more triggers, such as smoke, perfume, and other allergens. Viral illnesses are also a possible trigger, particularly in children. The narrowing of the airway causes symptoms such as wheezing, shortness of breath, chest tightness, and coughing. The airway constriction responds to bronchodilators. Between episodes, most patients feel well but can have mild symptoms and they may remain short of breath after exercise for longer periods of time than an unaffected individual. The symptoms of asthma, which can range from mild to life threatening, can usually be controlled with a combination of drugs and environmental changes. The estimated prevalence of asthma in the US adult population is 10%, so it represents a significant public health issue. As for HF and COPD, the disease is marked by sudden exacerbations.

A key marker of asthma is peak expiratory flow (PEF)—this can be obtained from the patient by asking them to blow into a spirometer. However spirometry only gives point measurements of function, and also requires the active involvement of the subject, and so is not suited for young children. Researchers have previously noted a link between PEF and respiratory rate. Accordingly what is needed is a system and method for monitoring respiratory rate in subjects with asthma.

Furthermore other disease conditions such as cystic fibrosis, pneumonia, corpulmonale and infection caused by the respiratory syncytial virus (RSV) may all be better monitored by a system capable of monitoring respiratory rate and/or nocturnal heart rate.

SUMMARY

This disclosure provides various embodiments of an apparatus, system, and method for monitoring subjects with chronic disease, using measurements of physiological function such as respiration, heart rate and other clinical measurements. The typical users of the system are (a) a person with a chronic disease, and (b) a caregiver with clinical expertise responsible for co-ordination of care for the person being monitored.

In one embodiment, a system for monitoring a subject is described, in which the system comprises a sensor configured to output a signal comprising a measured respiratory parameter of the subject; an analyzer configured to receive the signal and to at least store, in a memory, a plurality of respiratory features derived from the respiratory parameter, and an analyzer which is configured to selectively combine the plurality of respiratory features to determine an output that provides a health assessment of the subject.

In another embodiment, a method for monitoring a subject is described, in which the method comprises measuring a respiratory parameter of the subject; generating a plurality of respiratory features derived from the respiratory parameter, and combining the plurality of respiratory features to calculate an output that provides a health assessment of the subject.

The system described herein provides earlier detection of changes to allow clinical intervention, and improves the detection of clinical deterioration in heart failure. Further, the system described herein works through accurate, cost-effective and convenient measurement and analysis of physiological parameters. The physiological basis of the utility of this system in heart failure management is based on the observations provided above with respect to the markers of clinical deterioration in heart failure.

Given the significance of night-time respiration in assessment of heart failure, the present disclosure overcomes limitations of conventional techniques for measuring respiratory patterns, and provides for the measurement of overnight respiratory patterns over prolonged periods of time in a manner which is convenient for the patient. Further, an improved system and method is provided for analysis of respiratory patterns in heart failure relevant for the prediction of clinical deterioration.

In addition to providing long-term monitoring of subjects with known chronic diseases as discussed above, the system and method described herein also suitable to provide diagnosis of whether a person has one of the chronic diseases described above (or other chronic diseases). In such cases, measurements and analysis are carried out as in the case of chronic disease monitoring, but diagnostic decisions are made on the basis of a limited number of night (or recording period) measurements.

BRIEF DESCRIPTION OF THE DRAWINGS

Embodiments of the disclosure will now be described with reference to the accompanying drawings in which the acronym "a.u." is placed on the graphs to represent "arbitrary units". The units for the signals described below for respiratory effort and heart rate can be calibrated to more meaningful units such as liters/minute (for respiratory tidal volume) or mm (for ballistocardiogram displacements on the skin).

FIG. 5A illustrates an episode of periodic breathing (Cheyne-Stokes respiration) in which respiratory effort amplitude oscillates over several minutes. FIG. 5B illustrates two apneas detected by the biomotion sensor shown in FIG. 2.

FIG. 7A shows how the respiratory envelope changes when a hypopnea occurs.

FIG. 8A is the respiratory envelope of a person with heart failure measured over a five minute period. FIG. 8B is the power spectral density of the respiratory envelope shown in FIG. 8A. FIG. 8C is the respiratory envelope of a person without heart failure measured over a five minute period. FIG. 8D is the power spectral density of the respiratory envelope shown in FIG. 8C.

DETAILED DESCRIPTION

Figure 1:
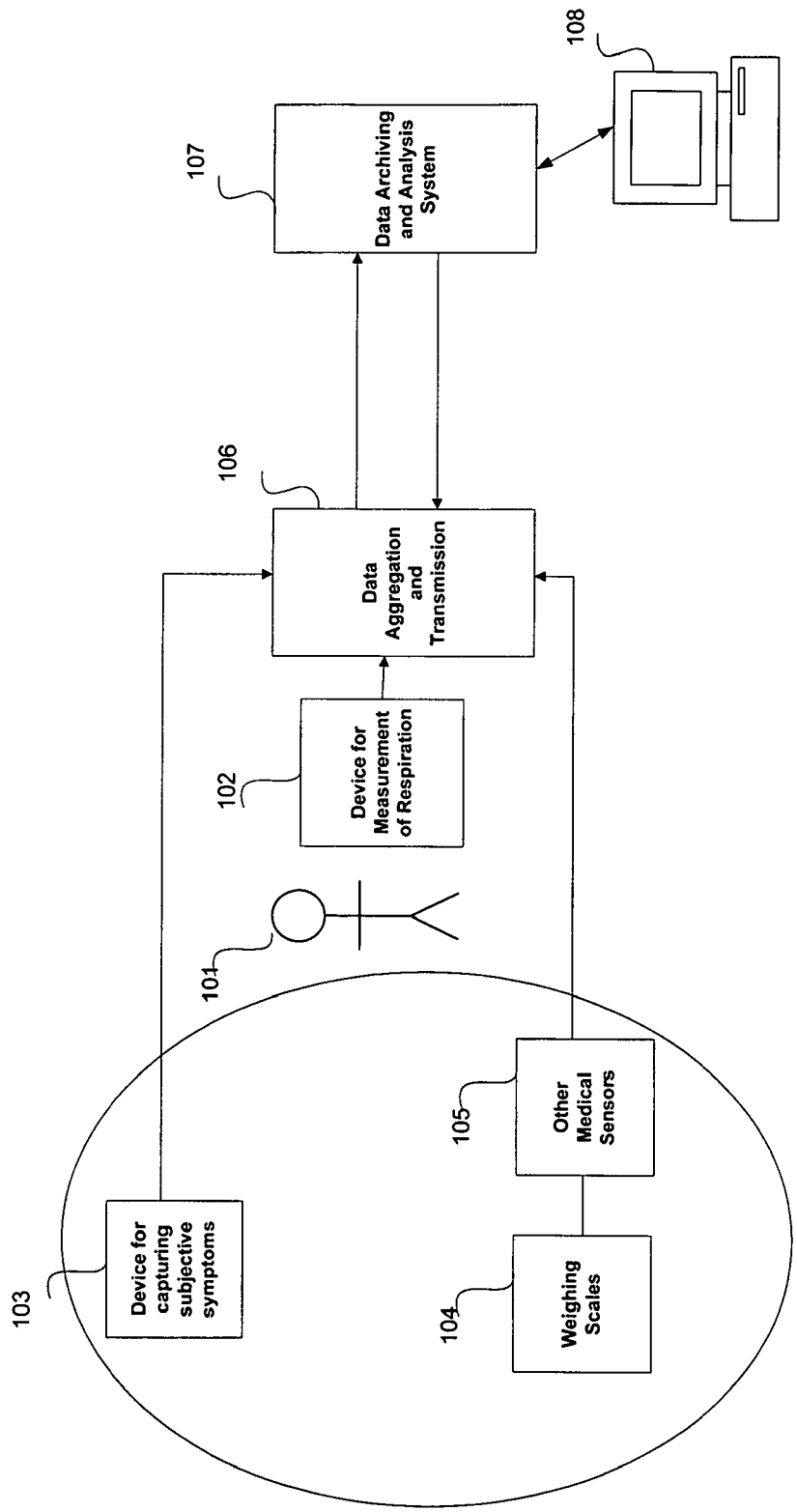
FIG. 1 is a diagram illustrating the overall schematic of an embodiment in which the subject is being monitored, together with devices for measuring respiratory patterns, heart rate and other physiological measurements. A device for capturing subjective symptom data is also depicted. It denotes the possibility of both local and remote archiving and analysis of the measurements.

FIG. 1 is a diagram illustrating the overall schematic of an embodiment of this disclosure. Subject 101 is monitored using respiratory sensor 102. Examples of respiratory sensors include abdominal inductance bands, thoracic inductance bands, a non-contact biomotion sensor, or an airflow sensor. The monitored respiration parameters can include respiratory effort, respiratory movement, tidal volume, or respiratory rate. Optionally device for capturing symptoms 103 can also be included. This could be as simple as a written diary, or could be an electronic data capture device which asks questions such as "do you feel breathless", "did you have discomfort breathing during sleep", "do you feel better or worse than yesterday", "do you feel your heart is racing", etc. One embodiment of such an electronic device could be a customized tablet PC, or alternatively a cell phone could be used, with voice-capture of subjective responses. The person's sleeping position could be obtained by asking a simple question such as "how many pillows did you use for sleeping", or through use of a position (tilt) sensor.

Orthopnea is a common symptom in heart failure. For simplicity, symptom questions could be restricted to requiring only simple yes/no responses. Optionally, further devices could be used to assess clinical status. Weight scale 104 has proven utility in monitoring heart failure through objective assessment of weight gain due to fluid retention. Other medical sensors 105 can be integrated such as ECG monitors, blood pressure monitors, point-of-care blood assays of BNP, spirometers (which can measure forced expiratory volume, and peak expiratory flow), oximeters (which can measure blood oxygen levels), blood glucose monitors, and point-of-care blood assays of C-reactive protein.

Measurements made from all the sensors mentioned above (respiration, weighing scales and other sensors) may be aggregated together in data aggregation device 106. Aggregation device 106 could be a cell-phone, a personal computer, a tablet computer, or a customized computing device. This aggregation device can also be referred to as a data hub and, at a minimum, it may transfer data from the respiratory sensor 102 to the aggregation device itself In one aspect of this embodiment, data aggregation device 106 may also have the capability of transmitting the collected data to remote data analyzer 107. Remote data analyzer 107 may itself be a server computer, personal computer, mobile computing device or another customized computing device. Remote data analyzer 107 will typically have storage, processing, memory and computational elements. Remote data analyzer 107 will typically be configured to provide a database capability, and may include further data archiving, processing and analysis means, and would typically have a display capability via display 108 so that a remote user (e.g., a cardiac nurse) can review data.

Figure 2:
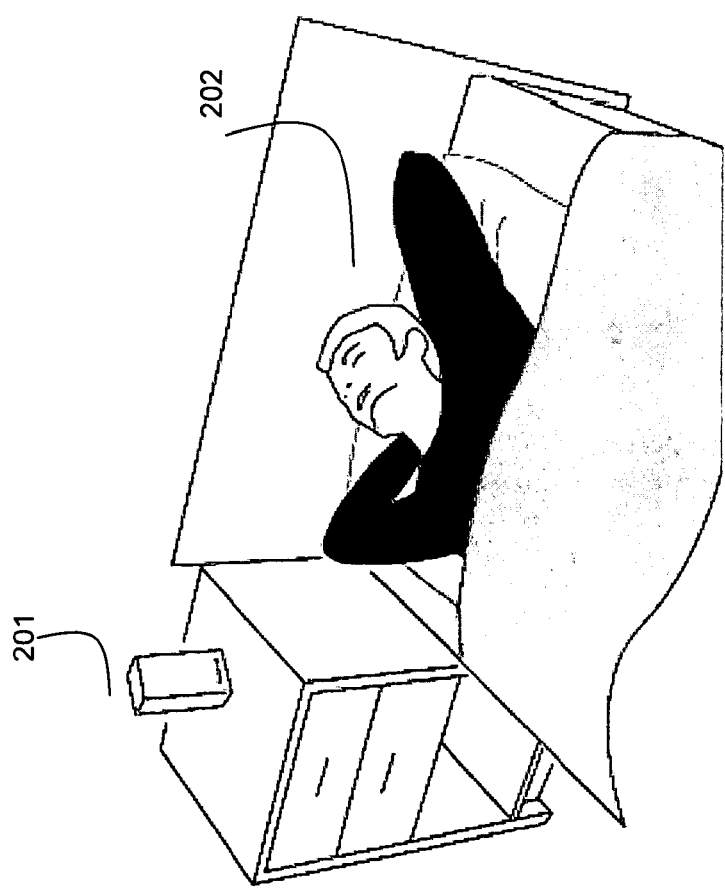
FIG. 2 illustrates a representative embodiment in which non-contact biomotion sensor is placed near the person being monitored. The motion signal can be used to derive respiration and heart rate patterns which are used as part of the chronic disease monitoring system.

FIG. 2 shows an embodiment of the respiration sensor, in which non-contact biomotion sensor 201 is used to monitor the respiratory effort and heart rate of a subject 202. This non-contact sensor is described in PCT Publication Number WO 2007/143535 A2 and U.S. Pat. No. 6,426,716, the entire contents of which are incorporated herein by reference. Non-contact sensor 201 is placed near the bed of the person 202 during sleep, and monitors movement. It operates by sending out a short impulse of radio-waves (in field-testing of this system, a frequency of 5.8 GHz is used with a pulse length of 5 ns). The reflection of this impulse is then mixed with a local delayed copy of the transmitted impulse. The mixer circuit outputs a signal which is related to the phase difference between the transmitted and received pulses-if the target is moving, this movement is modulated onto the phase signal. This phase signal is referred to as a raw movement signal. There are other non-contact motion sensor technologies which can be used analogously. Infra-red detection systems can be used to detect movement, as can ultrasonic transducers. To improve the sensitivity and robustness of a non-contact biomotion sensor, it is useful to have a quadrature detection system in which there are effectively two sensors with the base phase of their oscillations offset by n/4 radians. These two effective sensors can be implemented by using a single source oscillator, but whose base phase is modulated periodically by n/4 radians.

Figure 3:
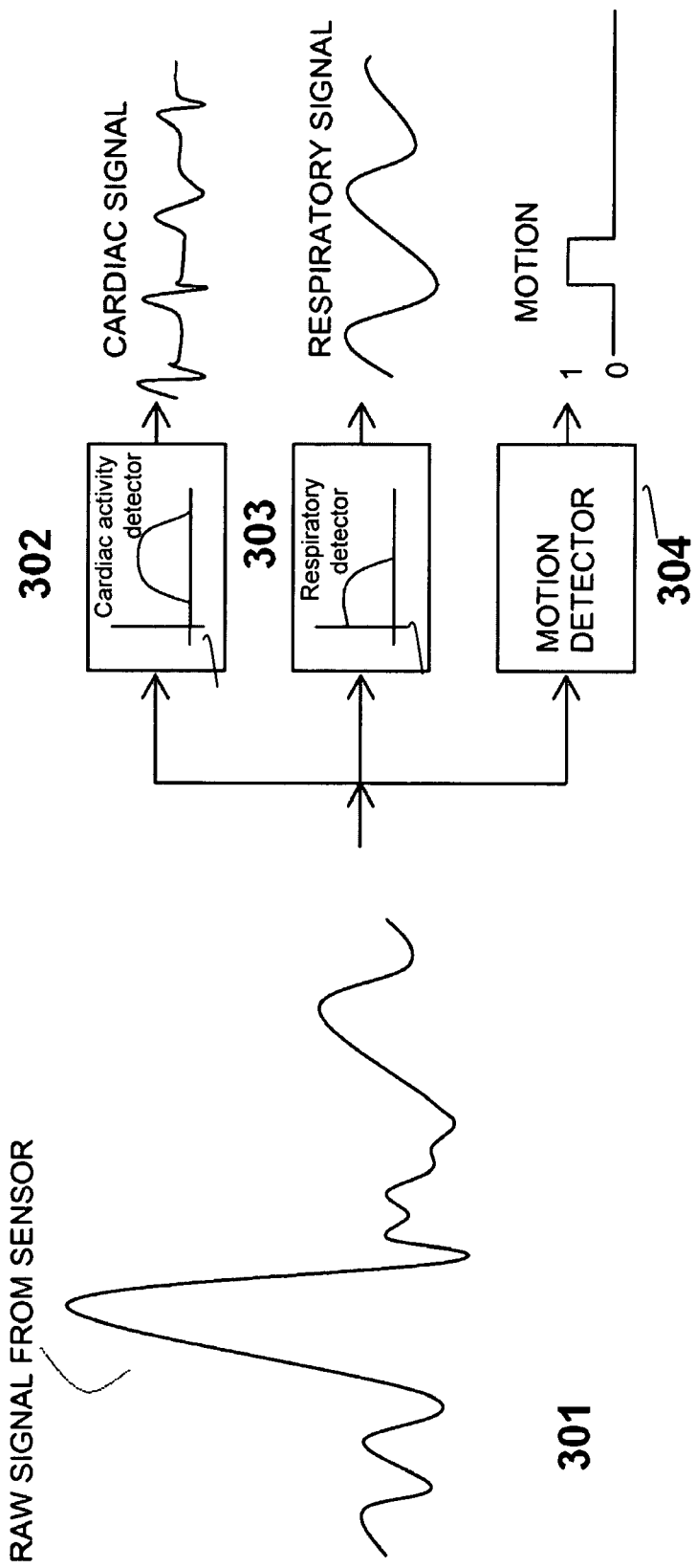
FIG. 3 shows how the raw motion signal derived from a bio-motion sensor can be decomposed into respiratory movements, cardiac movements, and movements associated with large bodily motion such as turning over or arm-movements.

FIG. 3 shows how the raw movement signal from biomotion sensor 301 can be decomposed into three components corresponding to significant bodily movement, respiratory effort and heart rate. Significant bodily movement would correspond to an action such as turning over, moving a leg, or twisting the head. Heart rate signal can be obtained using a cardiac activity detector 302 which in one embodiment is a bandpass filter applied to the raw movement signal. This bandpass filter preferentially passes signals in the region 0.5 to 10 Hz, which reflect heart rate signals. More elaborate processing such as preprocessing to remove movement and respiratory artifacts may be necessary. An alternative approach is to take an epoch of the raw signal and generate its power spectral density. Peaks in this spectral density (e.g., at 1 Hz) can be used to identify the average heart rate over that epoch (e.g., 1 Hz corresponds to 60 beats/minute). In this manner, a heart rate signal can be generated.

Similarly respiratory effort signal can be generated by a respiratory detector 303, which in one embodiment is a bandpass filter applied to the raw movement signal. This bandpass filter preferentially passes signals in the region 0.05 to 1 Hz which reflect respiratory signals. An alternative approach is to take an epoch of the raw signal and generate its power spectral density. Peaks in this spectral density (e.g., at 0.2 Hz) can be used to identify the average breathing rate over that epoch (e.g., 0.2 Hz corresponds to 12 breaths/minute). Finally, large bodily movements not related to respiration or cardiac activity can be identified using the motion detector 304 which implements techniques for motion detection 304. One method for detecting motion is to high-pass filter the raw movement signal, and then threshold the absolute value of the filtered signal. A second method is to calculate the energy of the raw movement signal over short epochs (e.g., 2 seconds). If the amplitude of the energy exceeds a threshold, a movement is detected. The amplitude of the movement can be assessed by calculating the energy value in that epoch. In that way, an activity count can be assigned to short epochs. The movement signal is processed to determine when the subject is asleep.

Figure 4:
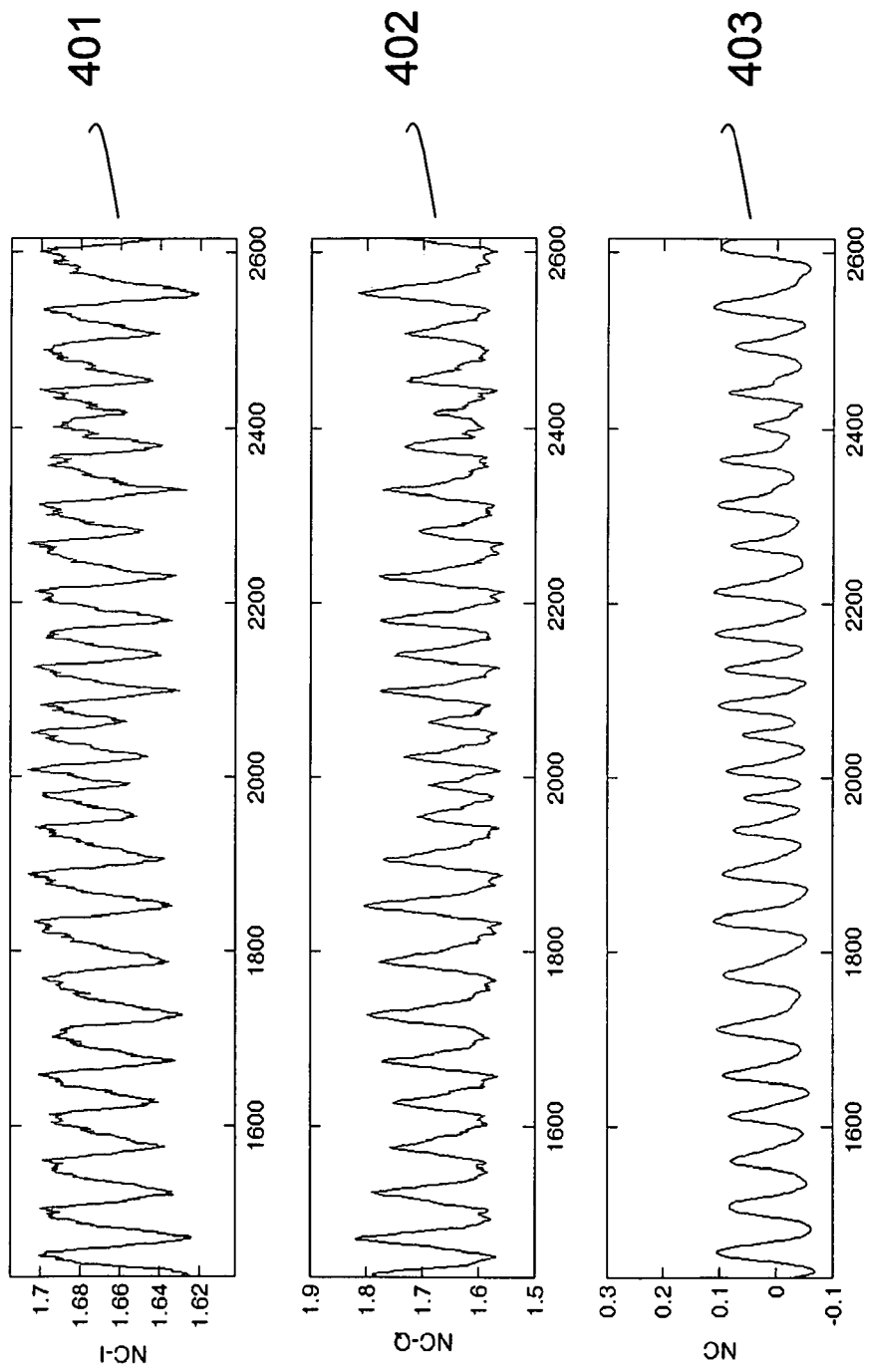
FIG. 4 illustrates how the process of phase demodulation applied to the I and Q signals obtained from a motion sensor can be used to derive a more accurate combined movement signal.

FIG. 4 gives an example of how to combine the I and Q signals obtained from the biomotion sensor. In this example, a technique called phase demodulation is employed. This is due to the fact that I signal 401 and Q signal 402 are not linearly correlated with the position of the moving subject, but rather represent the phase of the reflected signal. To compensate for this effect, the arcsine of the I channel, the arccosine of the Q channel and the arctangent of the I/Q ratio are calculated. This results in three potential output signals-one of these is chosen by calculating the overall amplitude of the signal, its signal-to-noise ratio, and its shape. The demodulated signal may then be low pass filtered to give the final respiratory movement signal 403. This process is only applied when the I and Q signals are believed to represent primarily respiratory movement.

Figure 5A:
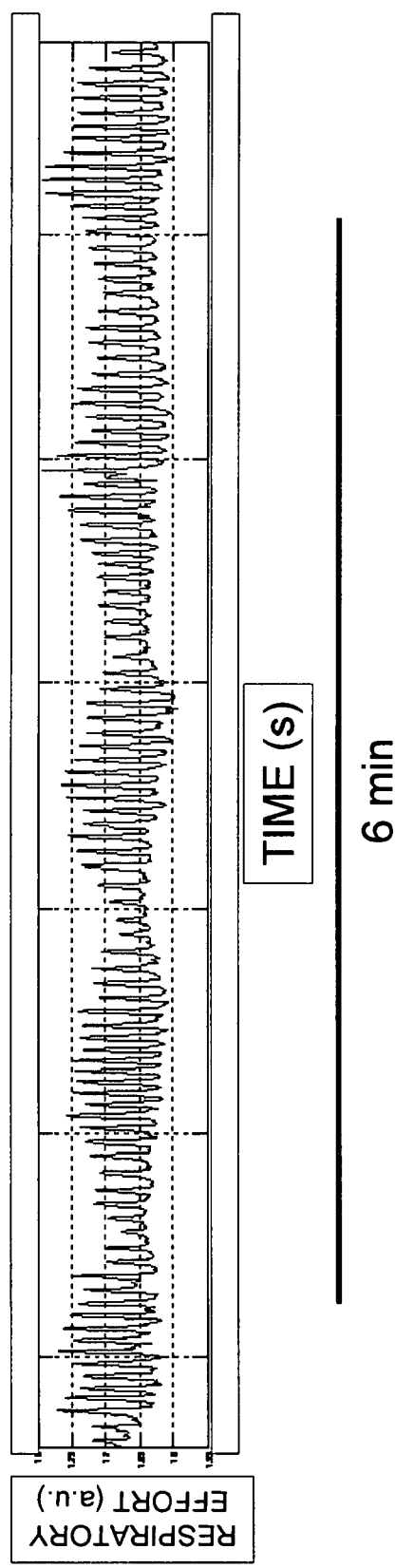
FIGS. 5A and 5B show examples of respiratory patterns which are used in the chronic disease monitoring system.
Figure 5B:
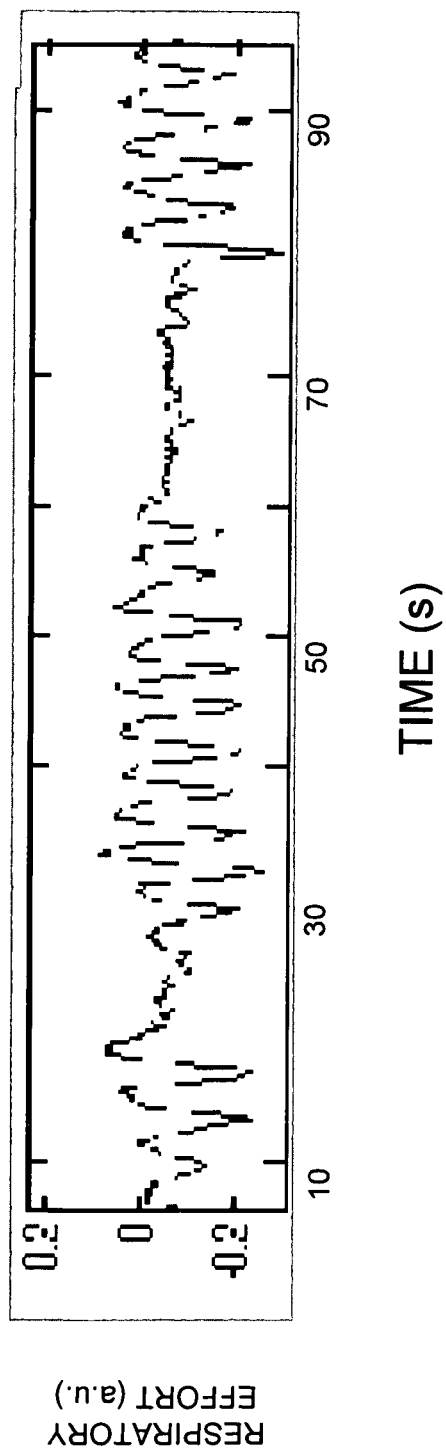

FIGS. 5A and 5B gives examples of breathing patterns measured in people suffering from chronic disease. FIG. 5A gives an illustration of what is known as Cheyne-Stokes respiration or periodic breathing. In this type of breathing the person's respiratory effort increases and decreases periodically, with a time scale of 30-90 seconds, typically. It is caused by an instability in the control of the relative amounts of oxygen and carbon dioxide in the blood, and is commonly seen in patients with heart failure. FIG. 5B shows an example of another respiratory event seen in chronic disease—an obstructive apnea. In an obstructive apnea, the person's respiratory effort is diminished for 10-20 seconds, before breathing recommences.

Figure 6:
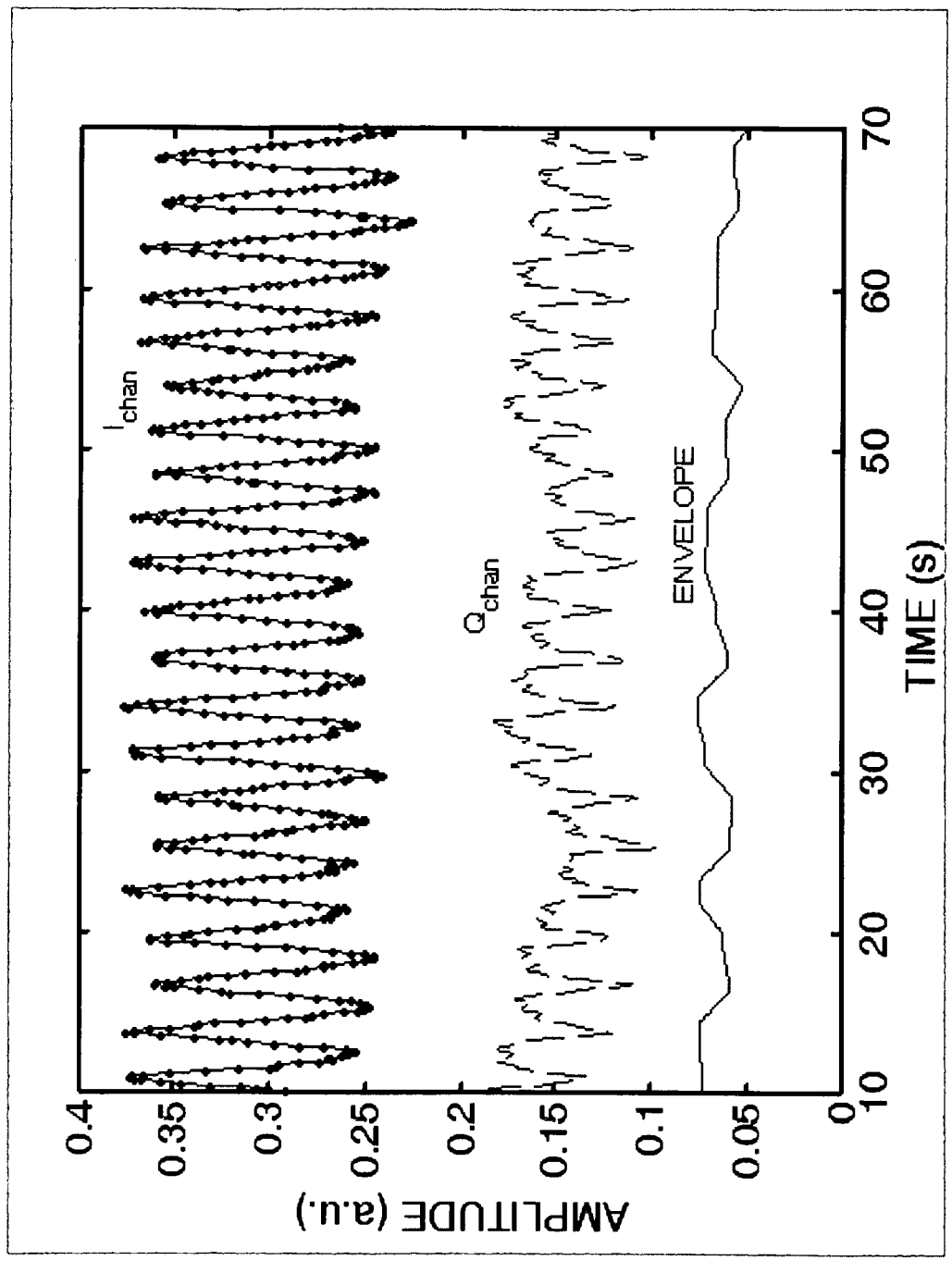
FIG. 6 shows two estimates of respiratory effort derived from biomotion sensor shown in FIG. 2 using quadrature (I and Q) signals and an envelope of the signal derived from the respiratory effort signals.

FIG. 6 is an illustration of a method for recognizing an apnea or hypopnea event from a respiratory signal, or set of signals. FIG. 6 shows that the non-contact biomotion sensor returns two signals associated with respiratory movement. These are the so-called I and Q quadrature signals. They may be generated by using radio-frequency pulses whose carrier waves are 90 degrees out of phase. The purpose of this is to smooth out the sensitivity response of the system. The I and Q channels both capture the respiratory movement, but with different amplitudes and phases. In order to obtain an "average" breathing signal, we combine the signals to form a single respiratory effort signal, R(t). One means to do this is to calculate $$R(t)=\sqrt{I^2(t)+Q^2(t)},$$

where I(t) and Q(t) represent the sampled values of the I and Q signals respectively. The envelope of this combined signal can then be obtained using a number of methods, for example, a "peak detect and hold" method, or a method using a Hilbert transform.

Figure 7B:
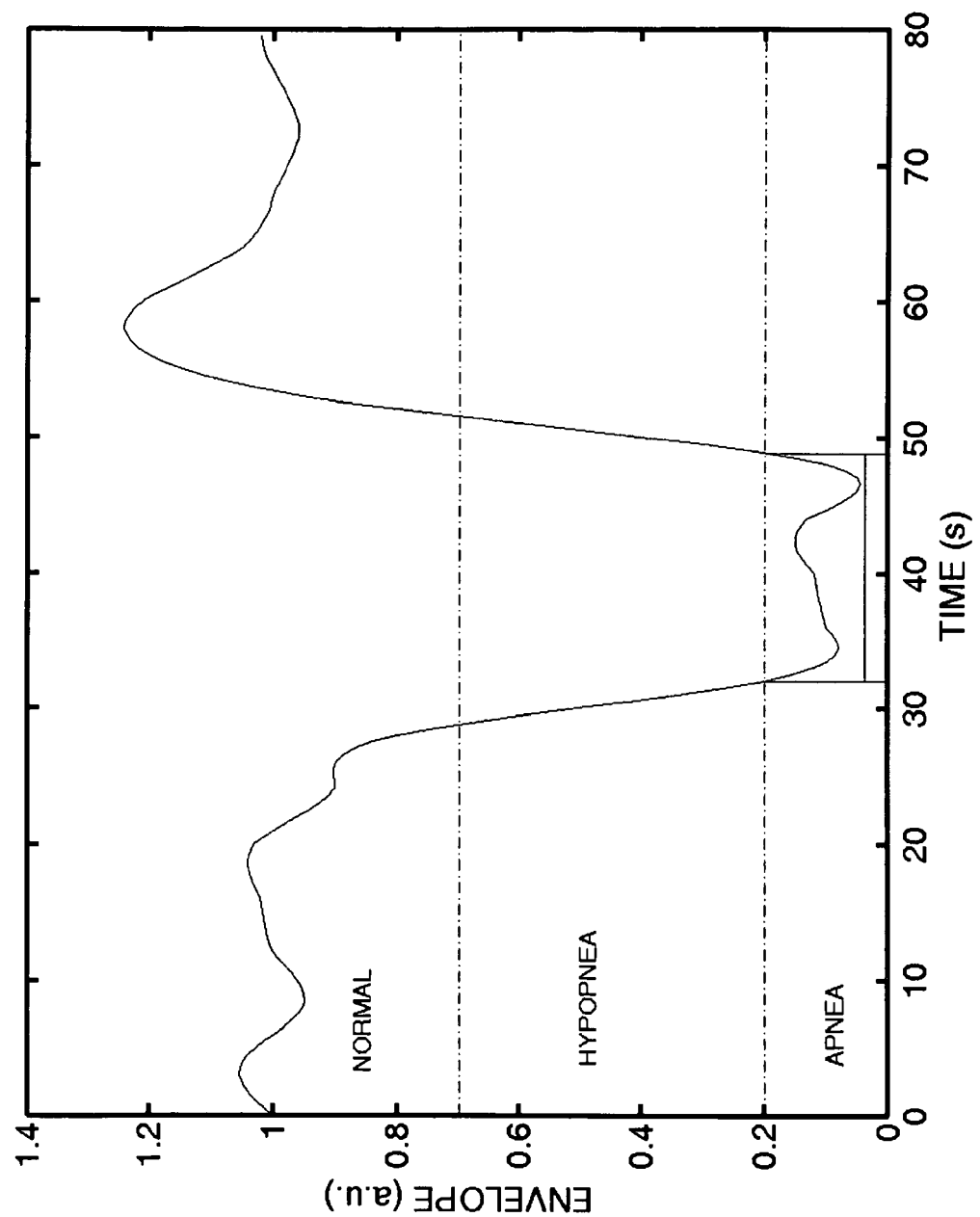
FIG. 7B shows how the respiratory envelope changes when an apnea occurs.

This respiratory envelope signal can then be processed to recognize apnea and hypopneas. As a specific embodiment, consider the results shown in FIGS. 7A and 7B. The respiratory envelope signal has been normalized over a period of multiple minutes, and its value is then shown over time. Using pre-established (or adaptive) rules, the amplitude of the respiratory envelope signal is compared to a number of thresholds. For example, in this case, if the amplitude stays above 0.7, breathing is considered normal. If the envelope stays between 0.2 and 0.7 for more than 10 seconds, then a hypopnea event is calculated. If the envelope dips below 0.2 for 10 seconds, then the event is considered an apnea. The person skilled in the art will realize that the exact rules will depend upon clinical definitions of apnea and hypopnea (which may vary from region to region), and the processing methods used for normalization and envelope extraction. In this way, specific events and their start and end times can be established. For example, FIG. 7A shows a hypopnea event which started at time t=18 s, and finished at t=31 s. FIG. 7B shows an apnea event which started at time t=32 s and ended at t=49 s.

An apnea-hypopnea index (AHI) is then calculated by counting the number of average number of apneas and hypopneas per hour of sleep (for example, if a person has 64 apneas, 102 hypopneas, and sleeps for 6.3 hrs, then their AHI is 166/6.3=26.3). This is an important parameter in assessing the overall status of the subject with chronic disease.

Figure 8A:
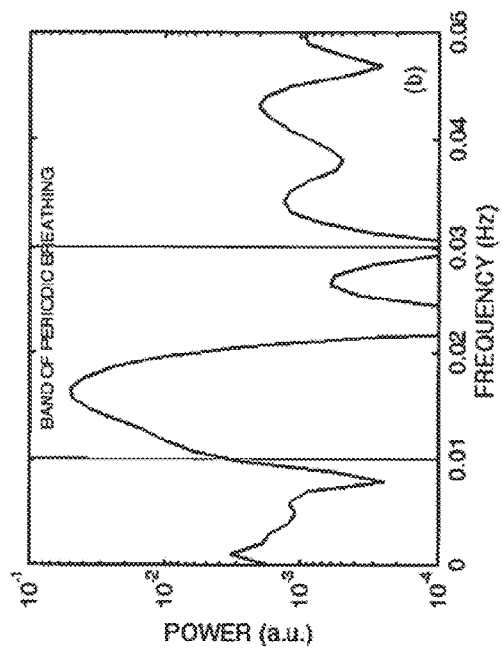
FIGS. 8A-8D show how the respiratory envelope changes over longer periods of time in the presence and absence of periodic breathing, including illustrating the power spectral densities of the respiratory envelopes in the presence of periodic breathing, and its absence.

It is also important in many chronic diseases to monitor episodes of periodic breathing (an example of which is shown in FIG. 5A). One embodiment of a method for detecting periodic breathing episodes may be implemented is as follows. The envelope of the respiratory signal is calculated as discussed in the previous paragraphs. FIG. 8A shows the respiratory envelope as a function of time over a period of approximately 5 minutes during which periodic breathing is present. The periodic breathing appears as a increase and decrease of the respiratory envelope over a time scale of about 80 seconds in this example.

Figure 8B:
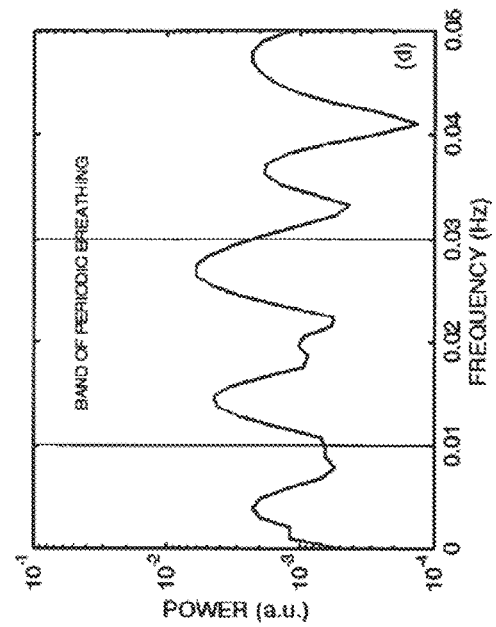
Figure 8C:
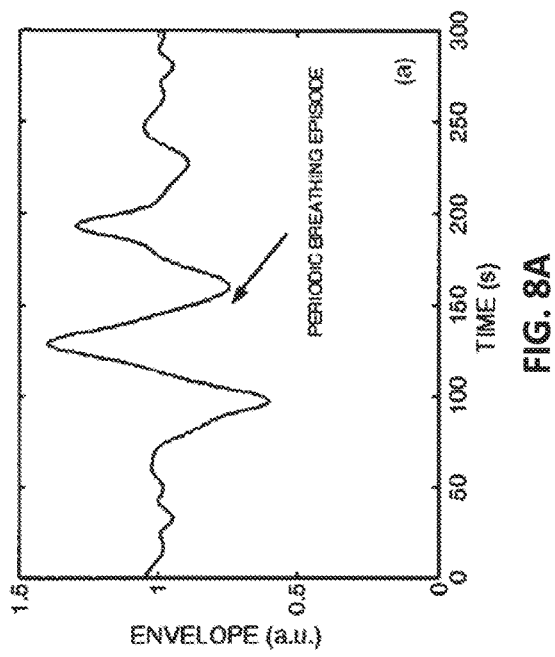
Figure 8D:
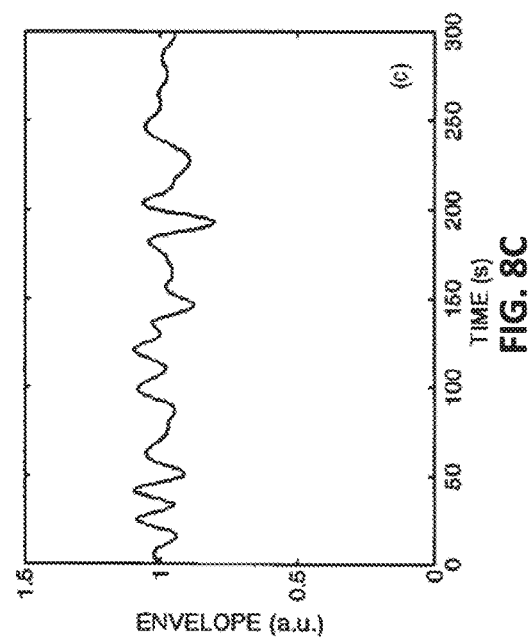

FIG. 8C shows a similar time period for the respiratory envelope during which no periodic breathing occurs. In order to recognize the periodic breathing episode, the power spectral density of the envelope signal for the 5-minute period is calculated. This is shown in FIG. 8B for the periodic breathing signal, and in FIG. 8D for the normal breathing segment. The periodic breathing will cause a significant modulation of the envelope at frequencies between 0.01 and 0.03 Hz approximately (i.e., characteristic time scales of 33 to 100 s). A threshold algorithm can then be used to determine whether the modulation is sufficient to be considered a periodic breathing episode. The 5 minute period can then be marked as a periodic breathing segment. In this way episodes of periodic breathing are determined. The total number of 5-minute segments so identified can be used to estimate the duration of periodic breathing. The person skilled in the art will realize that the exact rules for determining periodic breathing (Cheyne-Stokes respiration) will depend upon clinical definitions of periodic breathing (which vary from region to region), and the processing methods used for normalization, spectral density estimation and envelope extraction.

In this way, the total duration of periodic breathing per night can be determined, e.g., a person might have 22 minutes of periodic breathing in total on a particular night.

Figure 9A:
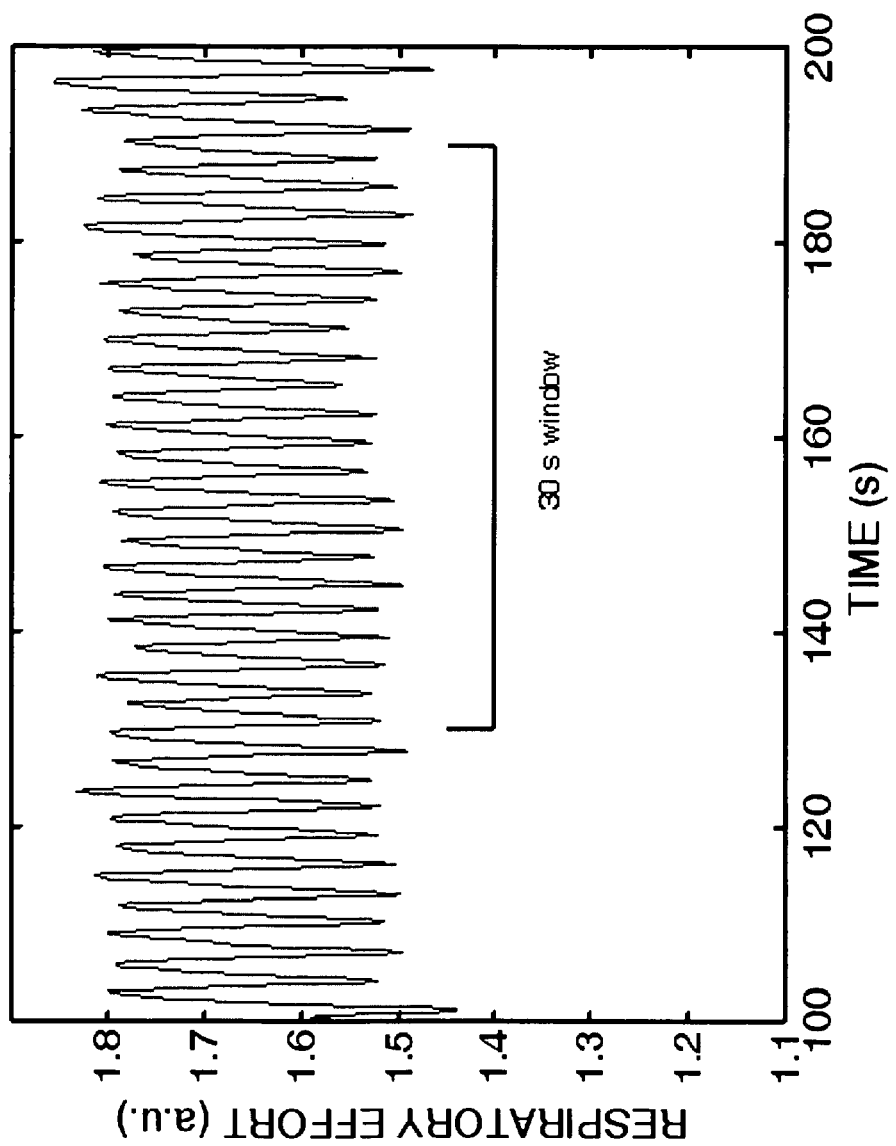
FIG. 9A shows an example of a respiratory effort signal recorded using the device shown in FIG. 2, and how the spectrum (FIG. 9B) of a 30-second epoch can be used to define respiratory rate.
Figure 9B:
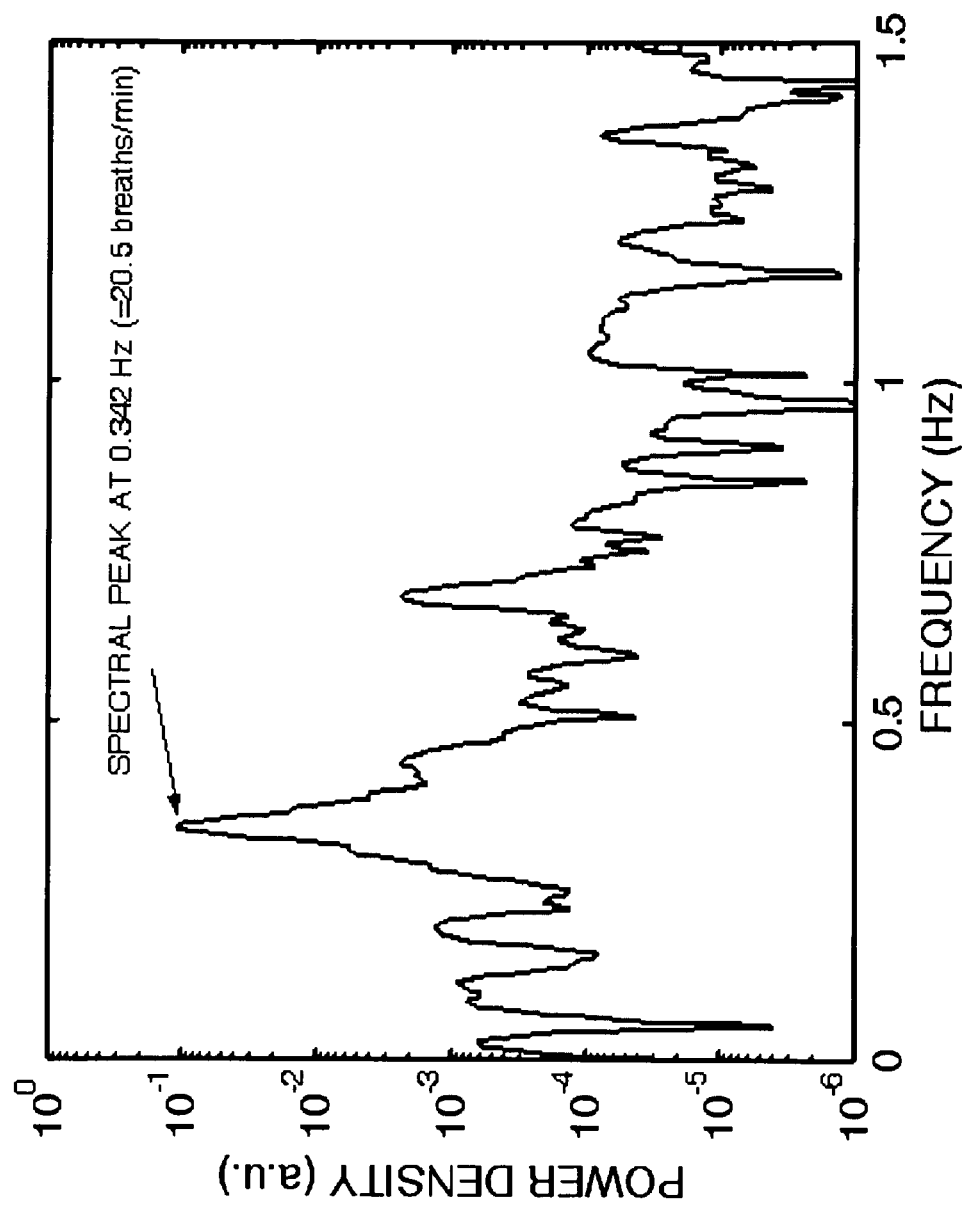

Monitoring the respiration rate itself is also an important parameter in chronic disease monitoring. For example, in acute respiratory failure the respiration rate can rise over 30 breaths/minute in adults, from a more typical baseline of 15 or 16 breaths/minute. One technique for tracking the respiratory rate during the night is as follows, as illustrated in FIG. 9A. For the case of a respiratory effort signal obtained from the non-contact sensor discussed earlier, a sliding window is applied to the data (e.g., 30 seconds in length). The power spectral density is then calculated for that epoch (FIG. 9B), using techniques such as the averaged periodogram. The power spectral density will typically contain a peak corresponding to the breathing frequency somewhere between 0.1 and 0.5 Hz This peak can be identified by using a peak-finding algorithm. In some cases, there may be excessive motion artifact on the data—in such a case a technique such as Lomb's periodogram can be used to estimate the power spectral density (this interpolates through missing data). Alternatively, the respiratory effort signal can be fit with a model using Auto Regressive or Auto Regressive Moving Average techniques. The model parameters can then be used to estimate the respiration frequency. Kalman filtering techniques can also be employed. In this way, an average respiration frequency for the time window can be obtained. The sliding window can then advance by 1 or more seconds. In this way, a time series of the respiration frequency can be build up over the night. A simple average respiration for the night can be obtained by averaging over this time series for the night. Alternatively, more complex measurements of respiratory frequency can be calculated such as median frequency, variance of the respiratory frequency, percentile distributions of the respiratory frequency, and auto-correlation of the respiratory frequency.

Figure 10:
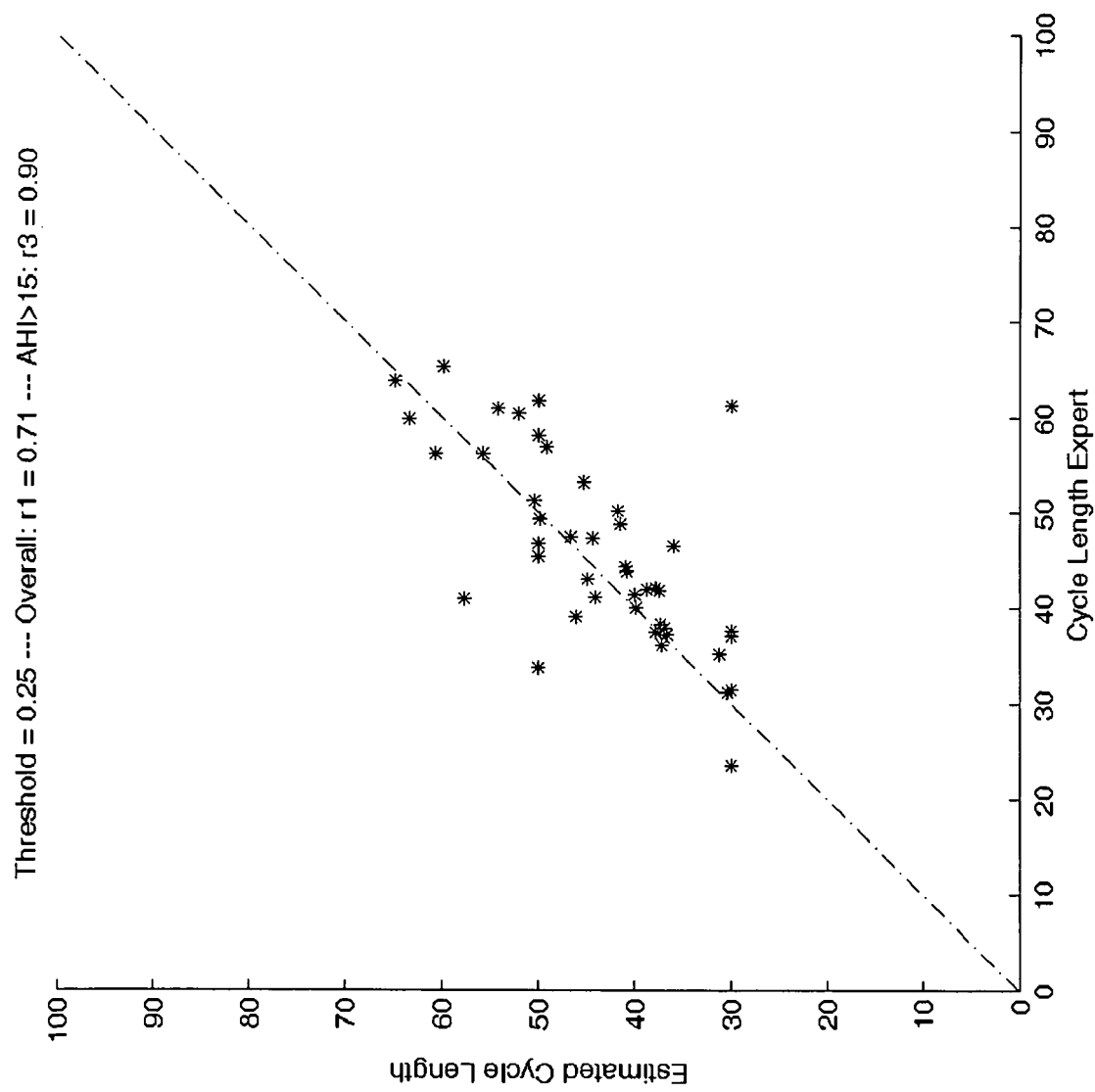
FIG. 10 shows an example of the agreement level between the characteristic modulation period of subjects with peri-odic breathing estimated using an algorithm based on the signals obtained from the sensor in FIG. 2, versus gold standard respiratory measurements using clinical polysomnogram measurements.

FIG. 10 shows an example of the calculated characteristic modulation periods in subjects with sleep apnea, using the signals obtained from a biomotion sensor, as compared to the periods calculated using the full respiratory effort and airflow signals obtained from a polysomnogram. This characteristic modulation period of Cheyne-Stokes respiration may have prognostic significance, as it is related to the circulation time. Circulation time refers to approximately the time it takes for blood to circulate throughout the complete cardiac system. It can be estimated by using the total circulating blood volume (Volume-liters) and cardiac output (CO, Volume/time—typically in liters/minute), so that the circulation time (CT) can be calculated as (blood volume/cardiac output). In normal adults, CT is typically about 20 seconds. Increases in central blood volume and/or reductions in cardiac output lead to a prolongation of circulation time. Increases in the circulation time cause feedback delay between the lungs and carotid chemoreceptors. When the circulation time in prolonged, it will take longer for ventilatory disturbances in the lungs to be sensed by the chemoreceptors. This delay leads to over- and undershooting of ventilation, and a periodic breathing pattern of the central or Cheyne-Stokes type. So in that manner, calculating the modulation period of Cheyne-Stokes respiration provides insight into the overall circulation time.

Figure 11:
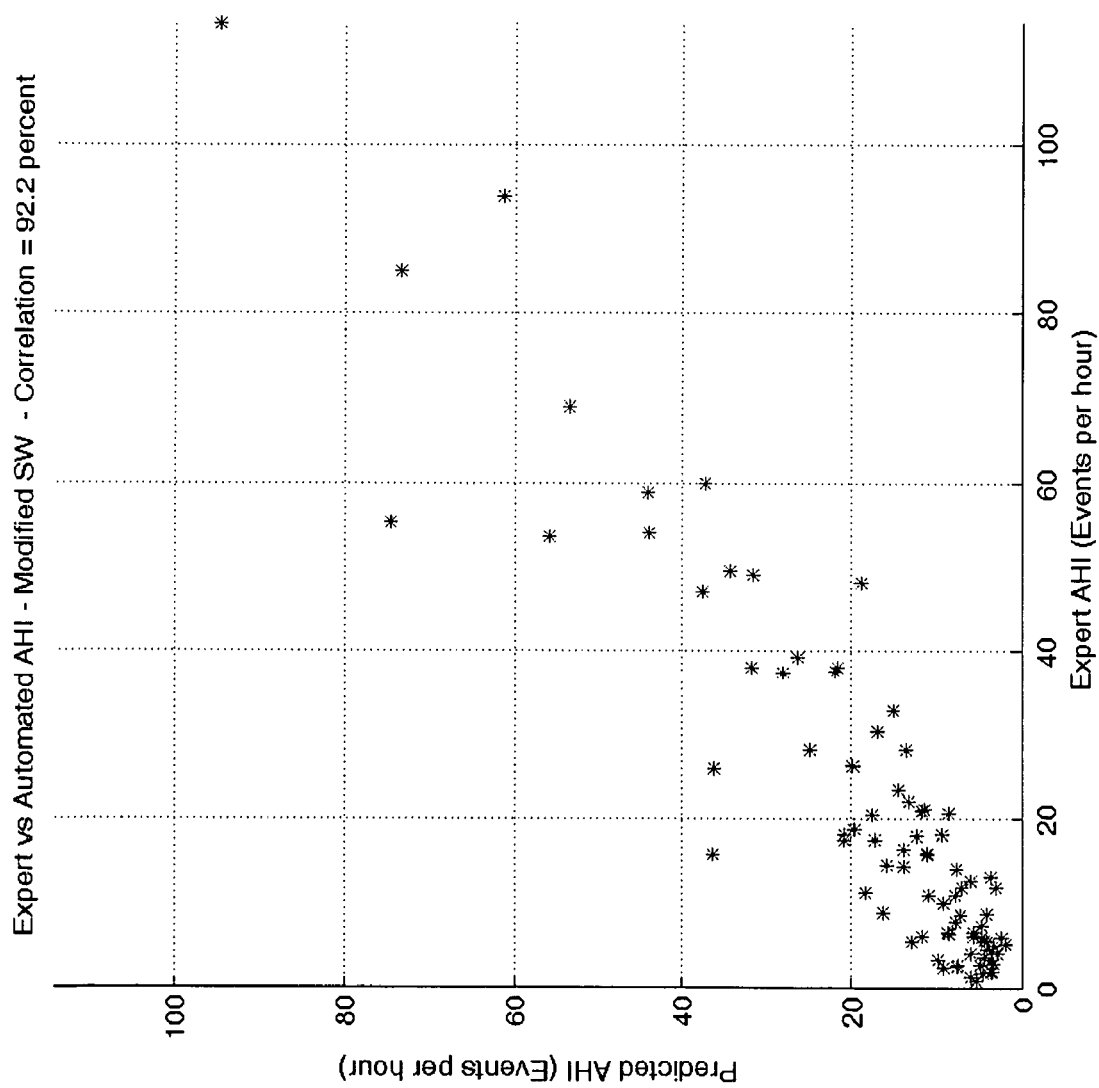
FIG. 11 shows an example of the agreement level between the estimated Apnea Hypopnea Index of subjects using an algorithm based on the signals obtained from the sensor in FIG. 2, versus gold standard respiratory measurements using clinical polysomnogram measurements.

FIG. 11 shows an example of the agreement level between the estimated Apnea Hypopnea Index (AHI) of subjects using an algorithm based on the signals obtained from the sensor in FIG. 2, versus "gold standard" respiratory measurements using clinical polysomnogram measurements. This is based on measurements from 85 nights, and shows a high level of agreement. AHI is known to have prognostic significance in subjects with heart failure.

Figure 12:
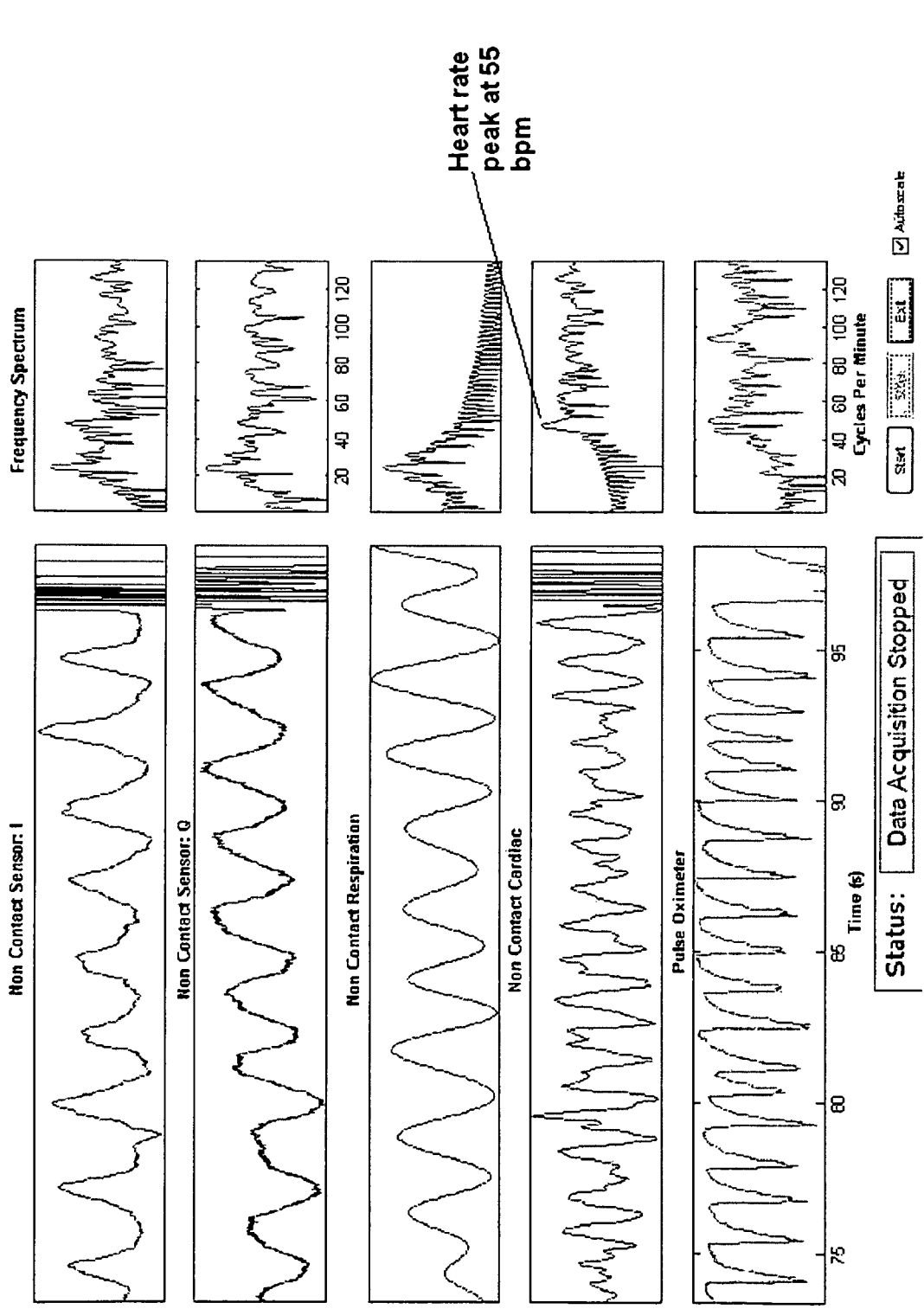
FIG. 12 shows how the non-contact biomotion sensor of FIG. 2 can also indicate heart rate as well as respiration rate.

Variations in nocturnal heart rate can also play an important role in determining a person's overall disease status. In an ideal scenario, the person's heart rate would be monitored in a simple non-intrusive fashion. In one implementation of the system, the non-contact biomotion sensor is used to also monitor the ballistocardiogram (the mechanical movement of the person's chest due to the beating heart). In FIG. 12, the signals measured using the non-contact biomotion sensor are pictured. A heart rate signal has been obtained by bandpass filtering of the received movement signal. Individual pulses are visible (see the fourth row of FIG. 12)—these can be compared with the pulses observed by a pulse oximeter (fifth row of FIG. 12). The average heart rate can be calculated by taking the power spectral density of the heart beat signal and looking for a peak in the range 45 to 120 beats per minute. In this case, the heart rate is about 55 beats per minute. The average nocturnal heart rate can be calculated by simple averaging of the measured heart rate over the time period from falling asleep to waking up. This heart rate can be determined from the non-contact sensor mentioned above, or other mechanisms such as a pulse oximeter, a chest band heart rate monitor, a clinical ECG, or a ballistocardiogram obtained from a pressure sensitive or charge sensitive mat.

Figure 13A:
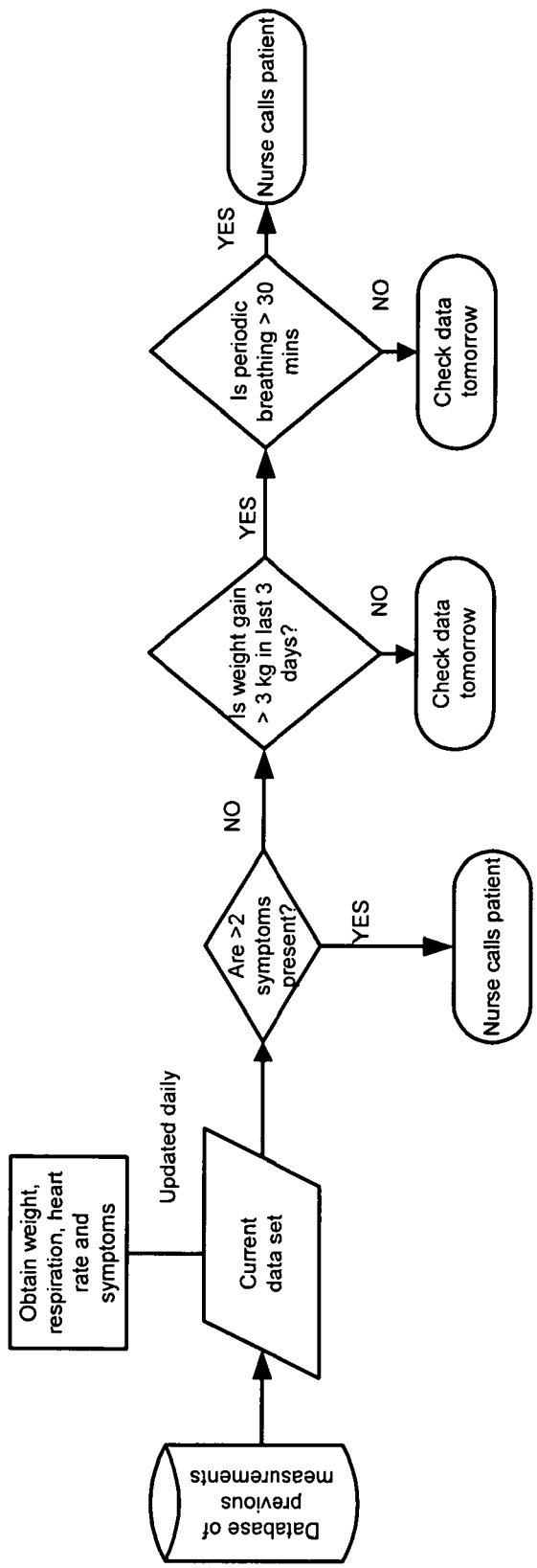
FIG. 13A illustrates a rule-based method for determining if a person with heart failure requires an intervention such as a nurse-call.

Prediction of clinical deterioration can then be obtained by using a predictive algorithm based on a classifier engine. The classifier can be rule-based, or a trained classifier such as a linear discriminant or logistic discriminant classifier model. In FIG. 13A, an exemplary embodiment of a rule-based classifier is shown. Various decisions are possible based on measurements from the patient, e.g., initiate a nurse call, monitor data more closely tomorrow, no-action, etc. These decisions are reached by applying rules to the measured data, and data that had been previously collected for that patient (or from other similar patients). Demographic information such as age and sex can form part of the previous data associated with that subject. For example, in FIG. 13A we show how the presence of two defined symptoms will always initiate a nurse call (e.g., the symptom questions might be "do you feel breathless" and "do you feel worse than yesterday"). In the absence of symptoms, the next rule to be applied could be to check if there has been a significant weight gain. If so, that could then initiate a check to see if there has been significant periodic breathing—if so then a nurse call will be made. The person skilled in the art will realize that these rules can be derived heuristically or using a number of machine learning algorithms.

Figure 13B:
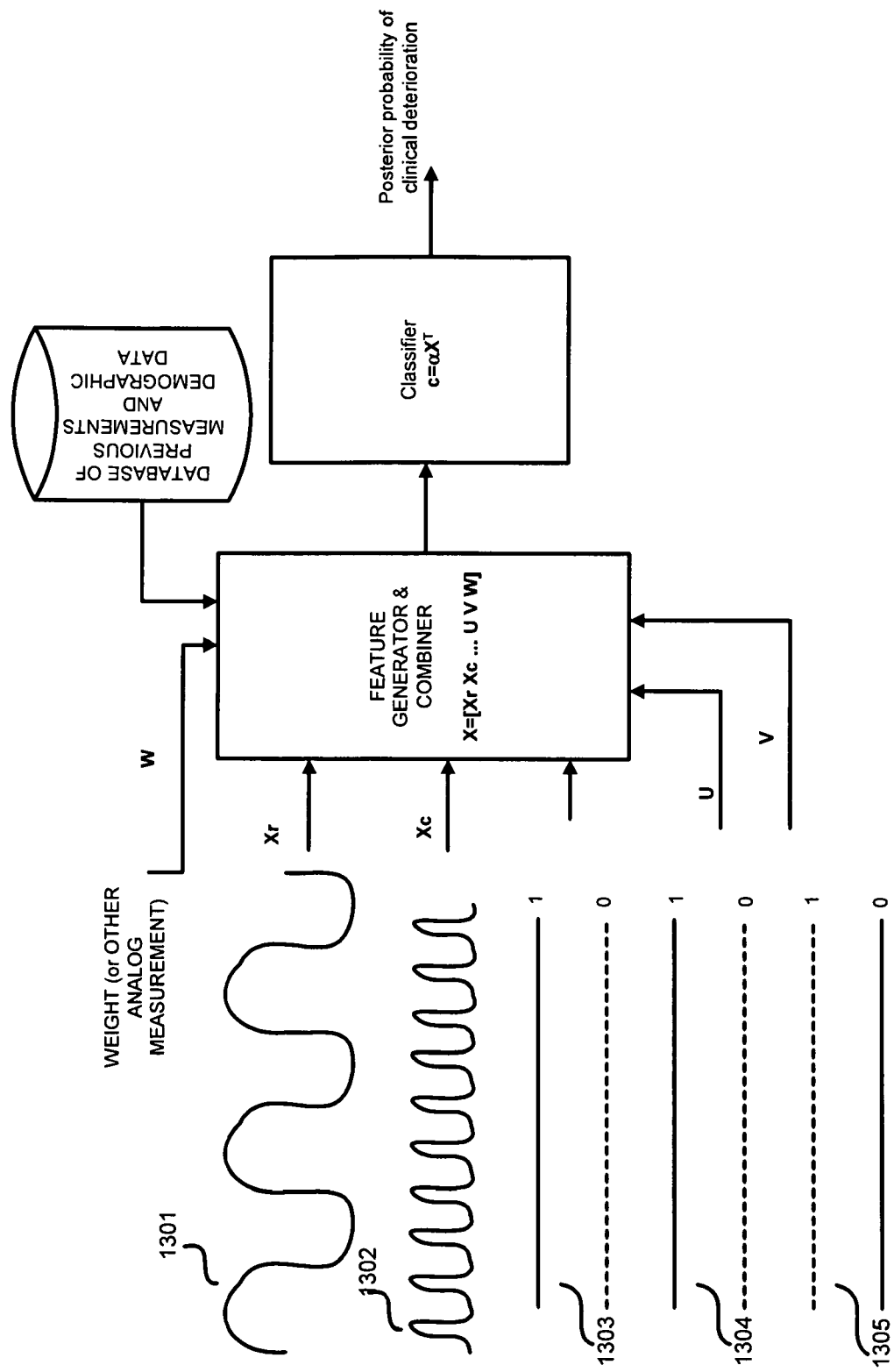
FIG. 13B illustrates a statistically based classifier approach to making a decision as to whether a person with a chronic medical condition has experienced a deterioration.

An alternative embodiment of the decision making process could be to use a more statistically based approach such as a classifier based on linear, logistic or quadratic discriminant as shown in FIG. 13B. In these approaches, the data from the respiration signal 1301 and cardiac signal 1302 is used to generate features (for example, the respiration features could be average nocturnal respiration rate, percentage of periodic breathing, variance of the respiration, etc.). Symptom input can be mapped to 0 or 1 (where 1 is a "yes" and 0 is a "no"). For example, the answer to the question "do you feel breathless" could map to a 0 or 1 and input as element 1303. The answer to the question "do you feel worse than yesterday" could map to element 1304. The answer to the question "did you use more than one pillow" could map to element 1305. Analog measurements such as weight or blood pressure could also be used to generate a "point" feature. Measurements from previous nights' recordings, and demographic features can also be included. The features from the various sources are then combined into a single vector X. The vector is then multiplied by a linear vector a, to produce a discriminant value c. This value is compared to a threshold to make a decision. The distance from the threshold can also be used to generate a posterior probability for a decision.

As a specific embodiment of a statistically based classifier, consider the exemplar where the feature vector X is composed as follows:

X=[AVERAGE RESPIRATORY RATE
  Δ(AVERAGE RESPIRATORY RATE) compared to AVG. OF LAST 5 NIGHTS
  90th PERCENTILE VALUE OF RESPIRATORY RATE
  VARIANCE OF RESPIRATORY RATE
  AVERAGE HEART RATE
  Δ(AVERAGE HEART RATE) compared to AVERAGE OF LAST 5 NIGHTS
  90th PERCENTILE VALUE OF HEART RATE
  Δ(WEIGHT) compared to AVERAGE OF LAST 5 NIGHTS
  RESPONSE TO "DO YOU FEEL BREATHLESS" (0 or 1)
  RESPONSE TO "DO YOU FEEL WORSE THAN YESTERDAY" (0 or 1)
  RESPONSE TO "DO YOU FEEL BREATHLESS WHEN LYING DOWN" (0 or 1)
  AGE
  GENDER (MALE=1, FEMALE=0)]

In this case, the feature vector has 13 elements. The linear row vector μ may take on the values
[1.4 3.1 0.8 1.2 1.3 2.4 0.9 3.2 4.1 2.5 3.4 0.1 0.2].
The values for a can be determined in a number of ways. One technique for calculating useful values of the parameters is to use a training data set of measurements and previous outcomes, and then optimize the parameters to most correctly predict the recorded outcomes. Note that the values of .alpha. will differ for different diseases. They may also vary across different patient groups, or even for individual patients. The feature vector X will also typically vary with disease category and patient group.

Based on data recorded from a specific night monitoring a patient, the product of .alpha.X might provide a discriminant value of c=34.7. This could be compared to a threshold of 30, where c>30 indicates clinical deterioration. The distance from the threshold represents the confidence of the decision that clinical deterioration has happened (e.g., if c=40, we are more confident that the person has clinical deterioration than if the value of c is only 31).

A person skilled in the art will realize that the values of the feature vector X can be obtained through prior training on a database of known values and outcomes, or can be made into an adaptive self-training algorithm.

Figure 14:
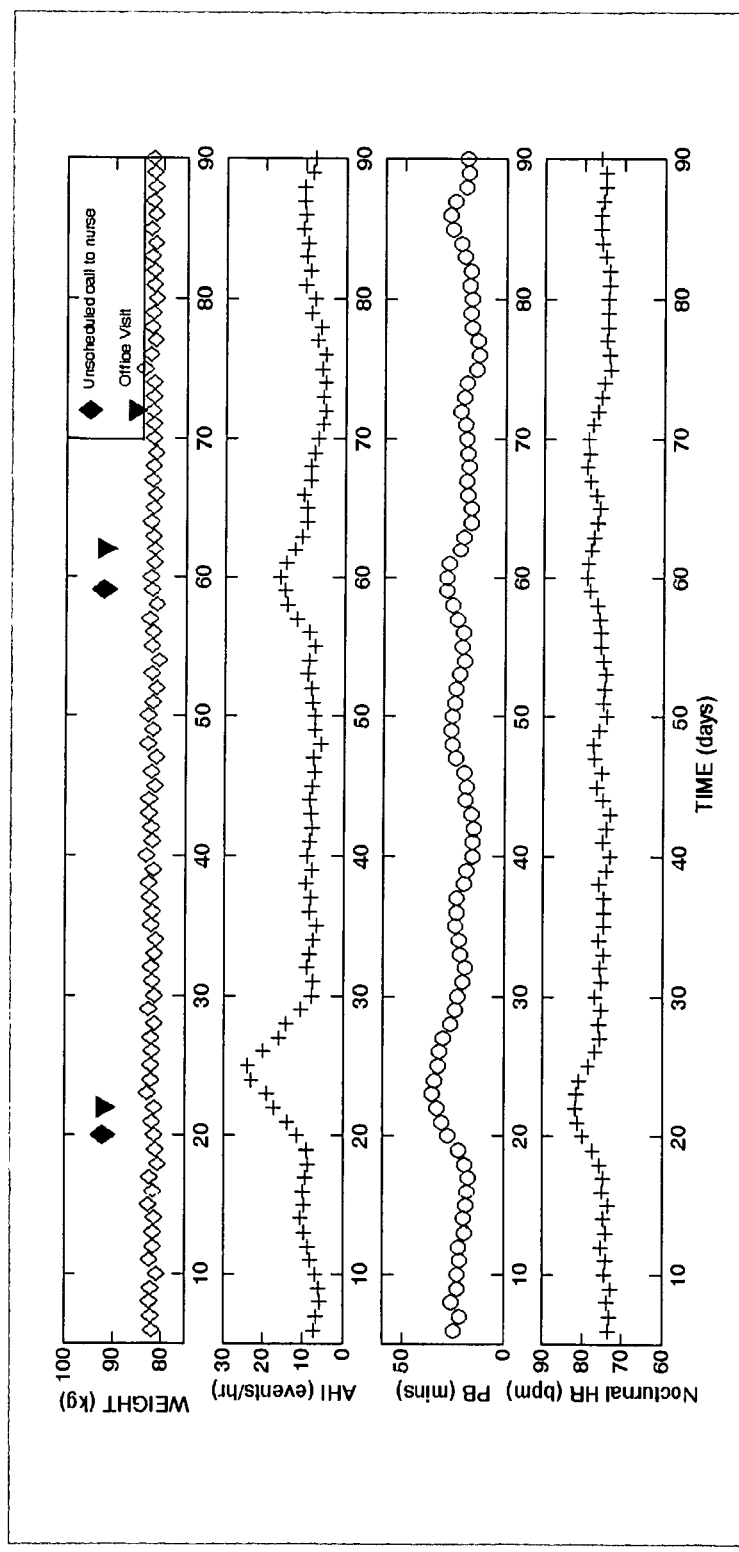
FIG. 14 shows an illustration of how the measurements from a person with chronic disease could be visualized over prolonger time periods (several weeks or months).

FIG. 14 shows an example of how the system may be used in the monitoring of a chronic disease. In this case, a person with heart failure is being monitored over a 90 day period. In this case, the subject is monitored using a respiratory sensor, a weighing scales and a device for measuring heart rate over some or all of the night. For each night of recording, the following parameters are recorded: (a) weight upon waking and after going to the bathroom (so called "dry weight"), (b) an estimated Apnea Hypopnea Index (AHI), (c) a periodic breathing index, and (d) an average nocturnal heart rate. Changes in these parameters can then be used to predict clinical events. For illustration, we have shown typical clinical events which were tracked in the development of the system—office visits to the heart failure clinic, and unscheduled calls to the nurse. The clinical prediction algorithms illustrated in FIGS. 13A and 13B are used to predict occurrences of events which require a nurse call.

Figure 15:
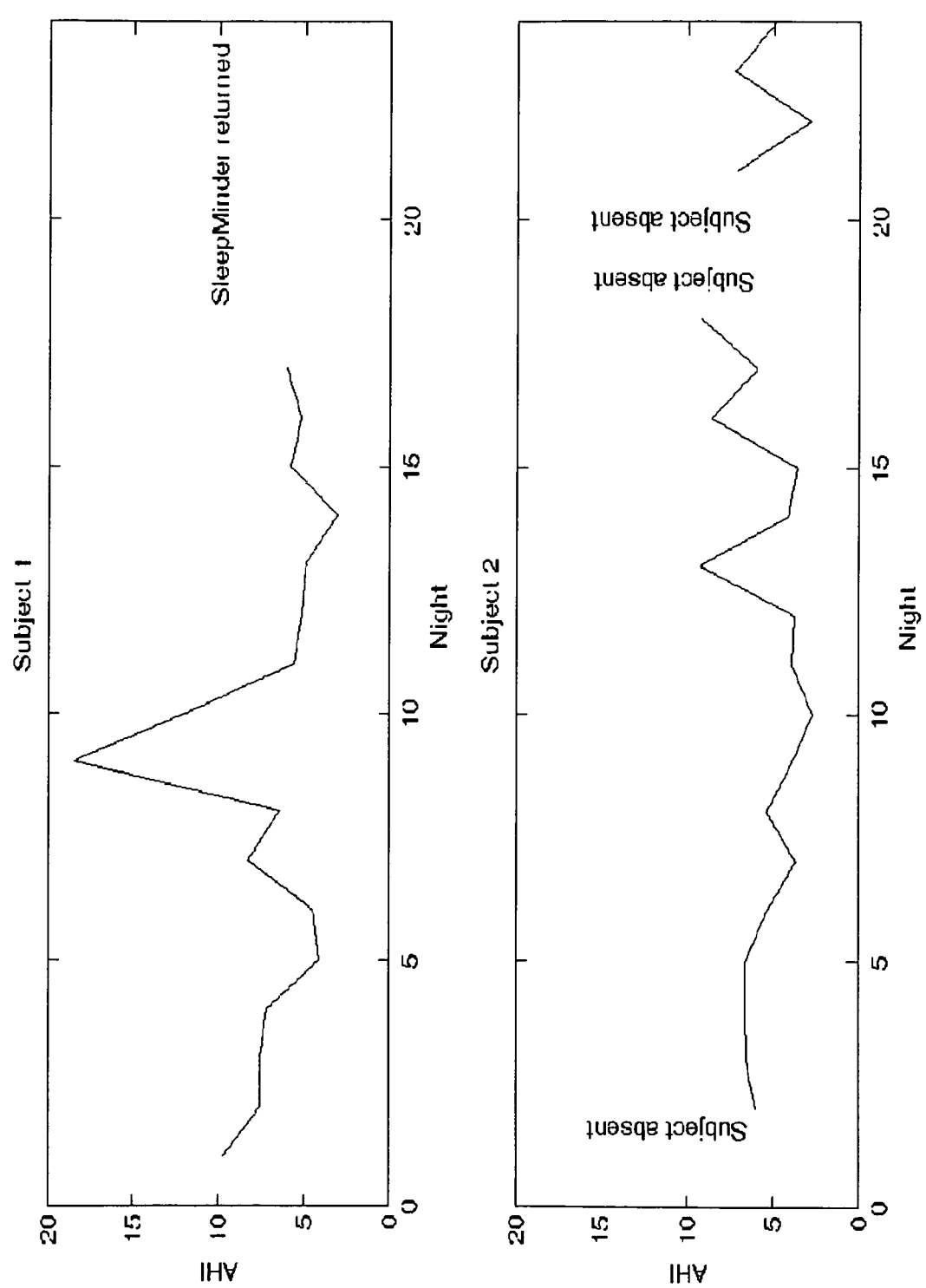
FIG. 15 shows an example of Apnea Hypopnea Indices measured in two subjects over approximate three week periods, using the system described in this specification.

FIG. 15 shows data obtained from two patients monitored over a n approximate 3-week period using the non-contact biomotion sensor shown in FIG. 2. It illustrates that the AHI does not vary significantly—this is consistent with the stable status of these subjects' heart failure during the trial period. The only exception is night 9 for subject 1 in which the AHI jumps to approximately 18 from a baseline of 5-10. This may have been due to a temporary worsening of symptoms due to excessive salt intake, or poor sleeping position, for example.

STATEMENT OF INDUSTRIAL APPLICABILITY

The apparatus, system and method of this disclosure finds utility in monitoring of subjects with chronic disease. In particular, it can be used to measure changes in clinical status which can be used as part of a clinical decision process.

The invention claimed is:

1. A system for monitoring a subject, the system comprising:
a sensor configured to receive signals reflected from the subject's body; and
an input device configured to receive user-generated responses from the subject,
the system being configured to:
generate, using one or more processors, respiratory movement data from at least one reflected signal received by the sensor;
derive, using the one or more processors, a respiratory effort envelope from the respiratory movement data;
derive, using the one or more processors, at least one respiratory parameter from the respiratory effort envelope, the at least one respiratory parameter comprising an apnea hypopnea index or a periodic breathing index;
implement, using the one or more processors, an automated classifier that combines the at least one respiratory parameter with at least one user-generated response received by the input device to determine a numerical value; and
provide, using the one or more processors, an output pertaining to a health assessment of the subject based on a comparison between the numerical value and a predetermined threshold.

2. The system of claim 1, wherein the one or more processors comprise one or more local processors further configured to pre-process the at least one reflected signal to generate the respiratory movement data.

3. The system of claim 2, wherein the one or more local processors are configured to implement the automated classifier.

4. The system of claim 1, wherein the one or more processors comprise one or more remote processors, wherein the system further comprises a transmitter configured to transmit the at least one respiratory parameter and the at least one user-generated response to the one or more remote processors, and wherein the one or more remote processors are configured to implement the automated classifier.

5. The system of claim 1, wherein the one or more processors comprise one or more remote processors, wherein the system further comprises a transmitter configured to transmit the at least one reflected signal and the at least one user-generated response to the one or more remote processors, and wherein the one or more remote processors are configured to generate the respiratory movement data, derive the respiratory effort envelope, derive the at least one respiratory parameter, and implement the automated classifier.

6. The system of claim 1, wherein the sensor is configured to transmit radio waves and receive transmitted radio waves reflected from the subject's body, and wherein the at least one reflected signal received by the sensor is a radio wave reflected from the subject's body.

7. The system of claim 1, further comprising:
a database that is configured to store the at least one respiratory parameter and the at least one user-generated response.

8. The system of claim 1, further comprising:
a display operatively coupled to the one or more processors such that a trend in the health assessment of the subject may be visualized.

9. The system of claim 1, wherein the automated classifier further combines one or more physiological parameters selected from the group consisting of: blood pressure, a forced expiratory volume, a peak expiratory flow, a blood oxygen level, a blood glucose level, a measurement of B natriuretic peptides, a measurement of C-reactive protein, significant bodily movement, and body weight, with the at least one respiratory parameter and the at least one user-generated response to determine the numerical value.

10. The system of claim 1, wherein the respiratory movement data is generated from a combination of two or more reflected quadrature signals received by the sensor.

11. The system of claim 1, wherein the system is further configured to determine, using the one or more processors, a proposed clinical intervention by applying a set of automated rules to the health assessment of the subject.

12. The system of claim 1, wherein the system is further configured to calculate, using the one or more processors, a likelihood of a clinical deterioration having occurred based on the comparison between the numerical value and the predetermined threshold.

13. The system of claim 1, wherein the at least one reflected signal comprises two or more components corresponding to respiratory effort and at least one of bodily movement or heart rate.

14. The system of claim 13, wherein the system is further configured to derive, using one or more processors, cardiac, and bodily motion parameters from the at least one reflected signal, and wherein the automated classifier further combines the cardiac and bodily motion parameters with the at least one respiratory parameter and the at least one user-generated response to determine the numerical value.

15. The system of claim 14, wherein the bodily motion parameter corresponds to a significant bodily movement.

16. The system of claim 1, wherein the at least one user-generated response includes symptom data from the subject.

17. The system of claim 1, wherein the at least one respiratory parameter comprises an apnea hypopnea index.

18. The system of claim 17, wherein deriving the apnea hypopnea index comprises comparing an overall amplitude of the respiratory effort envelope to one or more thresholds.

19. The system of claim 1, wherein the at least one respiratory parameter comprises a periodic breathing index.

20. The system of claim 19, wherein the periodic breathing index is derived from a power spectral density of the respiratory effort envelope.

21. The system of claim 1, wherein system is further configured to derive, using one or more processors, at least one additional respiratory parameter from the at least one reflected signal, wherein the at least one additional respiratory parameter comprises at least one of a respiratory rate, a respiratory effort, or a respiratory frequency, and wherein the automated classifier further combines the at least one additional respiratory parameter with the at least one respiratory parameter and the at least one user-generated response to determine the numerical value.

22. The system of claim 1, wherein the system is further configured to derive, using one or more processors, at least one respiratory frequency parameter from the at least one reflected signal, wherein the at least one respiratory frequency parameter comprises a median respiratory frequency, a variance of respiratory frequency, a percentile distribution of respiratory frequency, or an autocorrelation of respiratory frequency, and wherein the automated classifier further combines the at least one respiratory frequency parameter with the at least one respiratory parameter and the at least one user-generated response to determine the numerical value.

23. The system of claim 1, wherein the at least one user-generated response comprises demographic information.

24. The system of claim 23, wherein the demographic information includes the subject's age or sex.

25. The system of claim 1, wherein the automated classifier combines the at least one respiratory parameter with the at least one user-generated response, in part, by mapping the at least one user-generated response to at least one numerical quantity.

26. A method for monitoring a subject, the method comprising:
receiving, at a sensor, at least one signal reflected from the subject's body;
generating, by one or more processors, respiratory movement data from the at least one reflected signal;
receiving, at a data aggregation device, the at least one measurement of physiological data indicative of at least one physiological parameter of the subject;
receiving, at an input device, at least one user-generated response from the subject;
deriving, by the one or more processors, a respiratory effort envelope from the respiratory movement data;
deriving, by one or more processors, at least one respiratory parameter from the respiratory effort envelope, the at least one respiratory parameter comprising an apnea hypopnea index or a periodic breathing index;
implementing, by the one or more processors, an automated classifier that combines the at least one respiratory parameter with the at least one user-generated response to determine a numerical value; and
providing, by the one or more processors, an output pertaining to a health assessment of the subject based on a comparison between the numerical value and a predetermined threshold.

27. The method of claim 26, wherein the one or more processors comprise one or more local processors, and wherein the method further comprises:
pre-processing, by the one or more local processors, the at least one reflected signal to generate the respiratory movement data.

28. The method of claim 27, wherein the one or more local processors are used to implement the automated classifier.

29. The method of claim 26, wherein the one or more processors comprise one or more remote processors, wherein the method further comprises: transmitting the at least one respiratory parameter and the at least one user-generated response to the one or more remote processors, and wherein the one or more remote processors are used to implement the automated classifier.

30. The method of claim 26, wherein the one or more processors comprise one or more remote processors, wherein the method further comprises: transmitting the at least one reflected signal and the at least one user-generated response to the one or more remote processors, and wherein the one or more remote processors are used to generate the respiratory movement data, derive the respiratory effort envelope, derive the at least one respiratory parameter, and implement the automated classifier.

31. The method of claim 26, further comprising:
transmitting, from the sensor, radio waves,
wherein the at least one reflected signal received by the sensor is a radio wave reflected from the subject's body.

32. The method of claim 26, further comprising:
storing, in a database, the at least one respiratory parameter and the at least one user-generated response.

33. The method of claim 26, wherein the at least one user-generated response includes symptom data from the subject.

34. The method of claim 26, further comprising:
applying, by the one or more processors, a set of automated rules to the at least one respiratory parameter and the at least one user-generated response to output a proposed clinical intervention.

35. The method of claim 26, further comprising:
calculating, by the one or more processors, a likelihood of a clinical deterioration having occurred based on the comparison between the numerical value and the predetermined threshold.

36. The method of claim 26, wherein the output includes the health assessment and at least one of the at least one respiratory parameter or the at least one user-generated response.

37. The method of claim 26, further comprising:
deriving, by the one or more processors, at least one additional respiratory parameter from the at least one reflected signal, wherein the at least one additional respiratory parameter comprises at least one of a respiratory rate, a respiratory effort, or a respiratory frequency, and
wherein the automated classifier further combines the at least one additional respiratory parameter with the at least one respiratory parameter and the at least one user-generated response to determine the numerical value.

38. The method of claim 26, further comprising:
deriving, by the one or more processors, at least one respiratory frequency parameter from the at least one reflected signal, wherein the at least one respiratory frequency parameter comprises a median respiratory frequency, a variance of respiratory frequency, a percentile distribution of respiratory frequency, or an autocorrelation of respiratory frequency, and
wherein the automated classifier further combines the at least one respiratory frequency parameter with the at least one respiratory parameter and the at least one user-generated response to determine the numerical value.

39. The method of claim 26, wherein the at least one user-generated response comprises demographic information.

40. The method of claim 39, wherein the demographic information includes user age or sex.

41. The method of claim 26, wherein the at least one respiratory parameter comprises an apnea hypopnea index, and wherein deriving the apnea hypopnea index comprises comparing an overall amplitude of the respiratory effort envelope to one or more thresholds.

42. The method of claim 26, wherein the at least one respiratory parameter comprises a periodic breathing index, and wherein the periodic breathing index is derived from a power spectral density of the respiratory effort envelope.

* * * * *